(12) United States Patent
Foerster et al.

(10) Patent No.: US 7,090,690 B2
(45) Date of Patent: Aug. 15, 2006

(54) DEVICES AND METHODS FOR REPAIRING SOFT TISSUE

(75) Inventors: Seth A. Foerster, San Clemente, CA (US); Norman S. Gordon, Irvine, CA (US); Mark A. Ritchart, Murrieta, CA (US); Gregory H. Bain, Laguna Niguel, CA (US); George White, Corona, CA (US)

(73) Assignee: Arthrocare Corporation, Austin, TX (US)

( * ) Notice: Subject to any disclaimer, the term of this patent is extended or adjusted under 35 U.S.C. 154(b) by 0 days.

(21) Appl. No.: 10/299,171

(22) Filed: Nov. 19, 2002

(65) Prior Publication Data

US 2004/0098050 A1    May 20, 2004

(51) Int. Cl.
*A61B 17/04* (2006.01)
(52) U.S. Cl. ..................................... 606/232
(58) Field of Classification Search ................ 606/232
See application file for complete search history.

(56) References Cited

U.S. PATENT DOCUMENTS

| | | | |
|---|---|---|---|
| 4,946,468 A * | 8/1990 | Li ............................... 606/232 |
| 5,037,422 A * | 8/1991 | Hayhurst et al. ............. 606/72 |
| 5,046,513 A * | 9/1991 | Gatturna et al. ............. 128/898 |
| 5,330,442 A * | 7/1994 | Green et al. ................. 606/232 |
| 5,364,407 A | 11/1994 | Pol |
| 5,383,905 A | 1/1995 | Golds et al. |
| 5,464,427 A * | 11/1995 | Curtis et al. ................. 606/232 |
| 5,514,159 A | 5/1996 | Matula et al. |
| 5,584,835 A | 12/1996 | Greenfield .................... 606/73 |
| 5,630,824 A * | 5/1997 | Hart ............................ 606/139 |
| 5,702,397 A | 12/1997 | Goble et al. .................. 606/72 |
| 5,720,765 A | 2/1998 | Thal ............................ 606/232 |
| 5,733,307 A | 3/1998 | Dinsdale ..................... 606/232 |
| 5,791,899 A | 8/1998 | Sachdeva et al. |
| 5,868,789 A | 2/1999 | Heubner ..................... 606/232 |
| 5,980,559 A | 11/1999 | Bonutti ....................... 606/232 |
| 6,045,574 A | 4/2000 | Thal ............................ 606/232 |
| 6,086,608 A | 7/2000 | Ek et al. ...................... 606/232 |
| 6,200,329 B1 | 3/2001 | Fung et al. |
| 6,280,474 B1 | 8/2001 | Cassidy et al. |
| 6,475,230 B1 | 11/2002 | Bonutti et al. |
| 6,520,980 B1 | 2/2003 | Foerster |
| 6,527,794 B1 | 3/2003 | McDevitt et al. ............ 606/232 |
| 6,575,987 B1 * | 6/2003 | Gellman et al. ............. 606/151 |
| 6,585,730 B1 | 7/2003 | Foerster |
| 6,660,023 B1 | 12/2003 | McDevitt et al. ............ 606/232 |
| 6,855,157 B1 | 2/2005 | Foerster et al. |

* cited by examiner

Primary Examiner—Gary Jackson
(74) Attorney, Agent, or Firm—Rick Batt

(57) ABSTRACT

Devices and methods are disclosed for securing soft tissue to bone, and particularly for axially anchoring suture which attaches the soft tissue to adjacent bone structure.

20 Claims, 13 Drawing Sheets

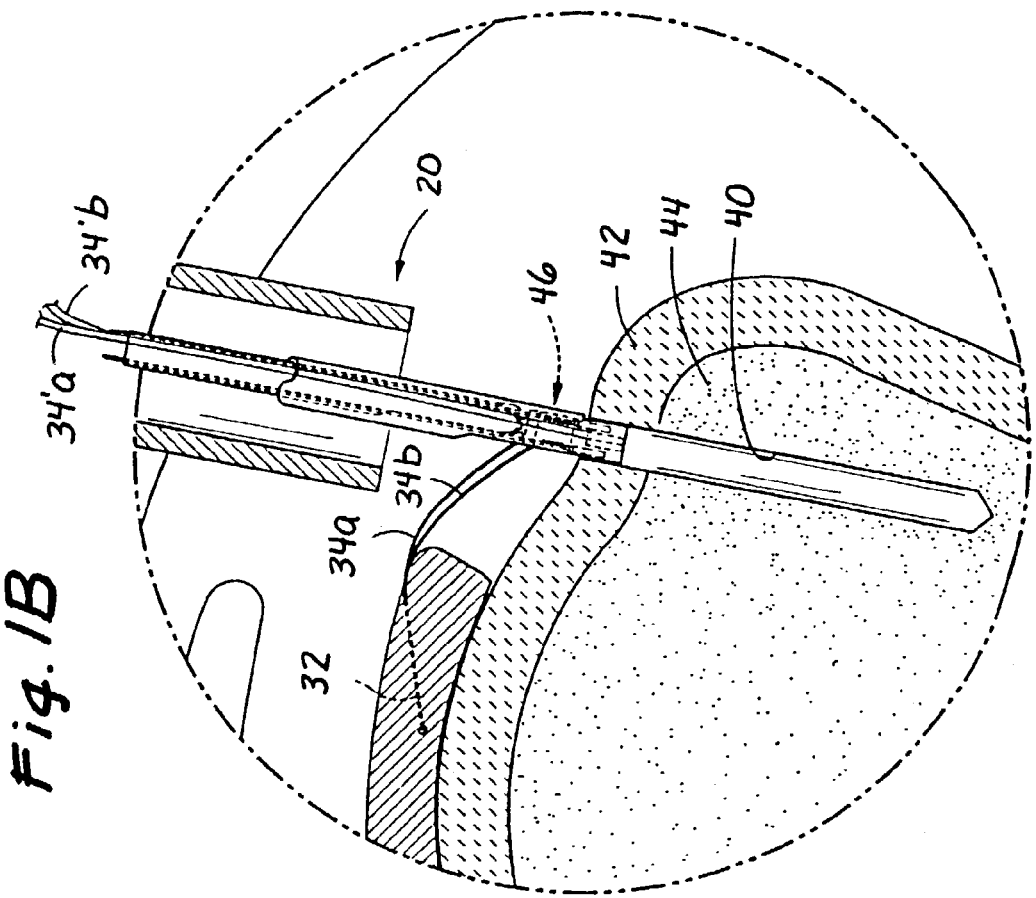
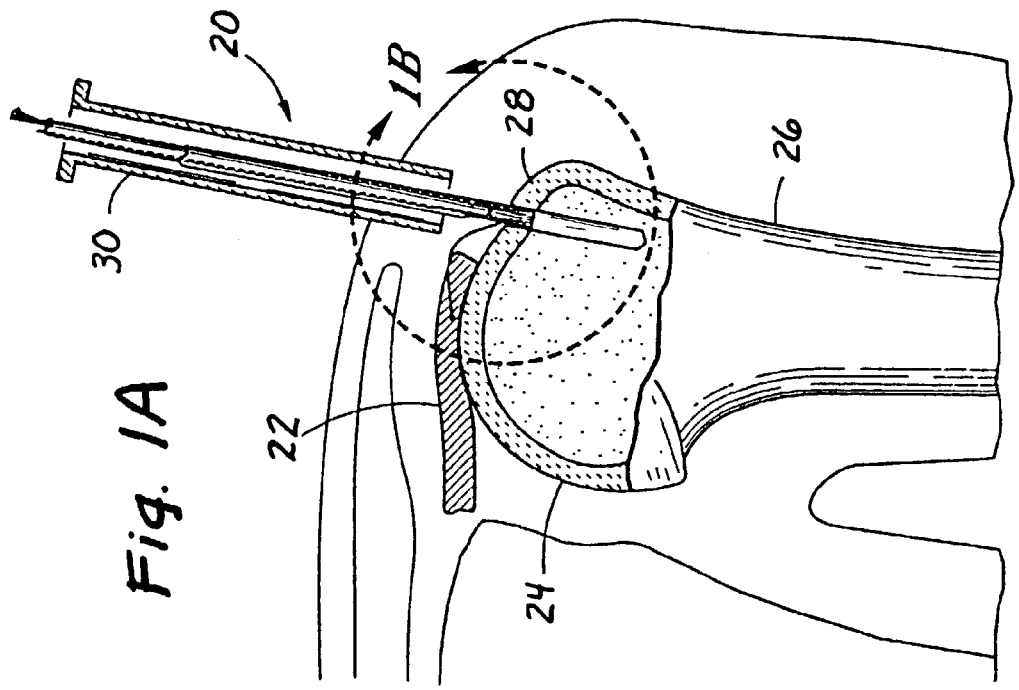

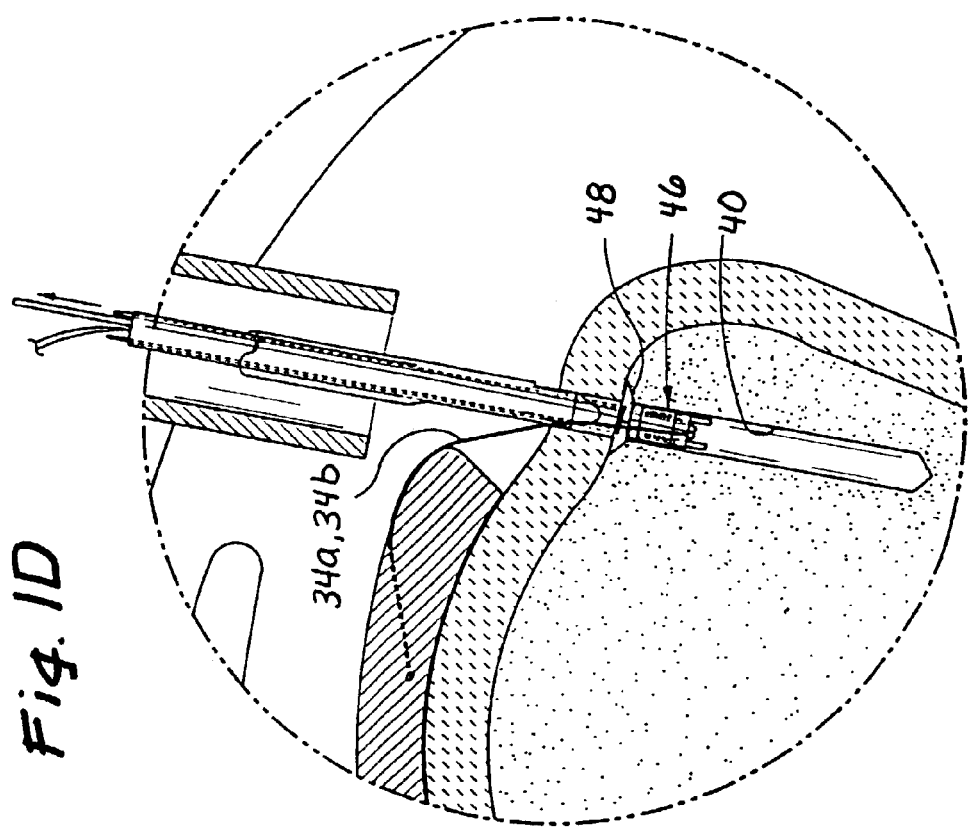
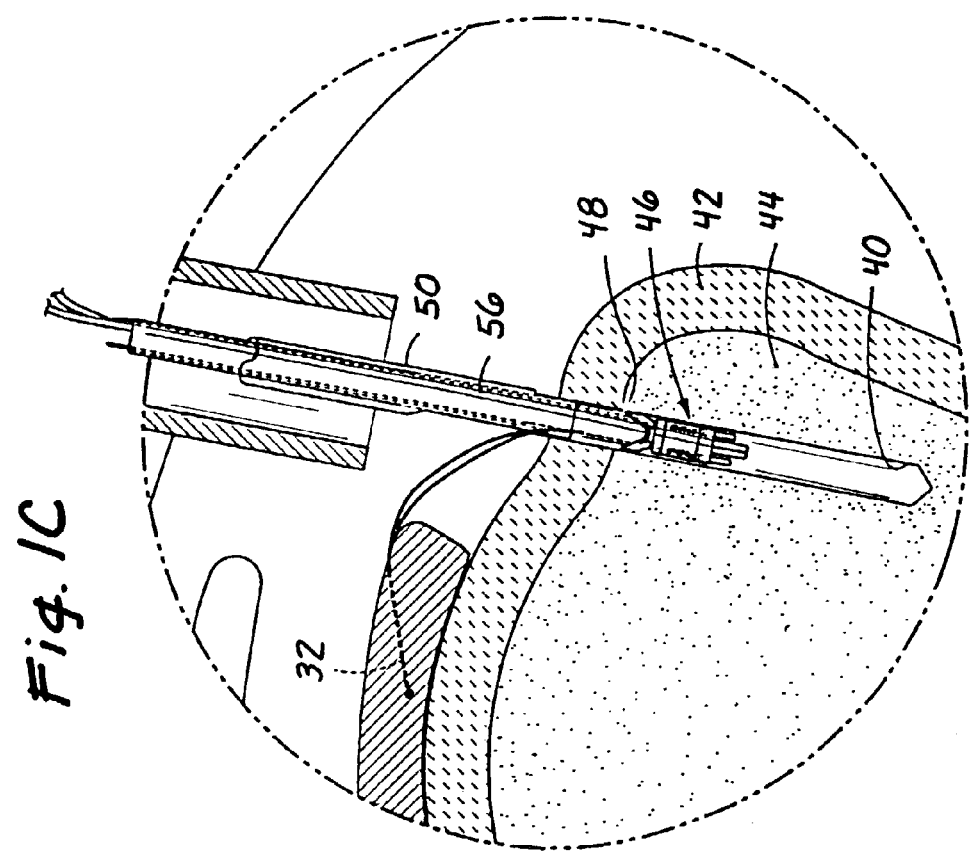

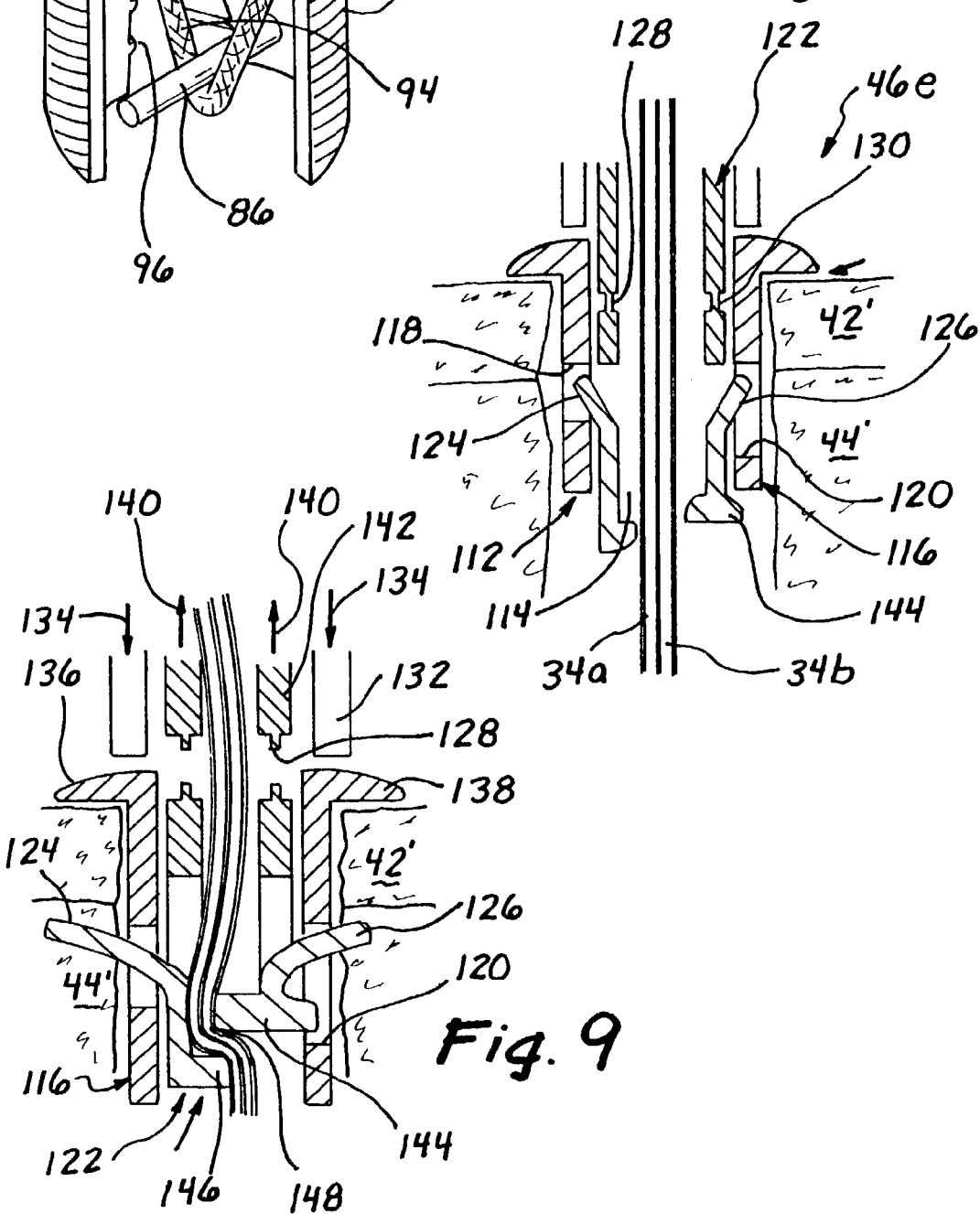

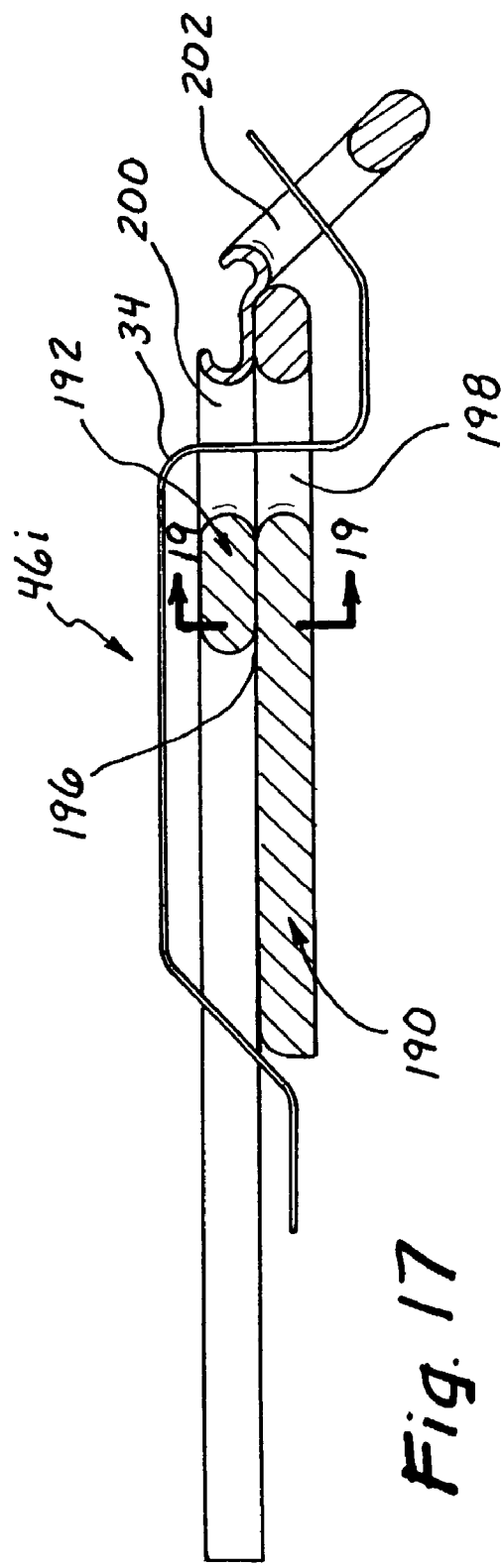
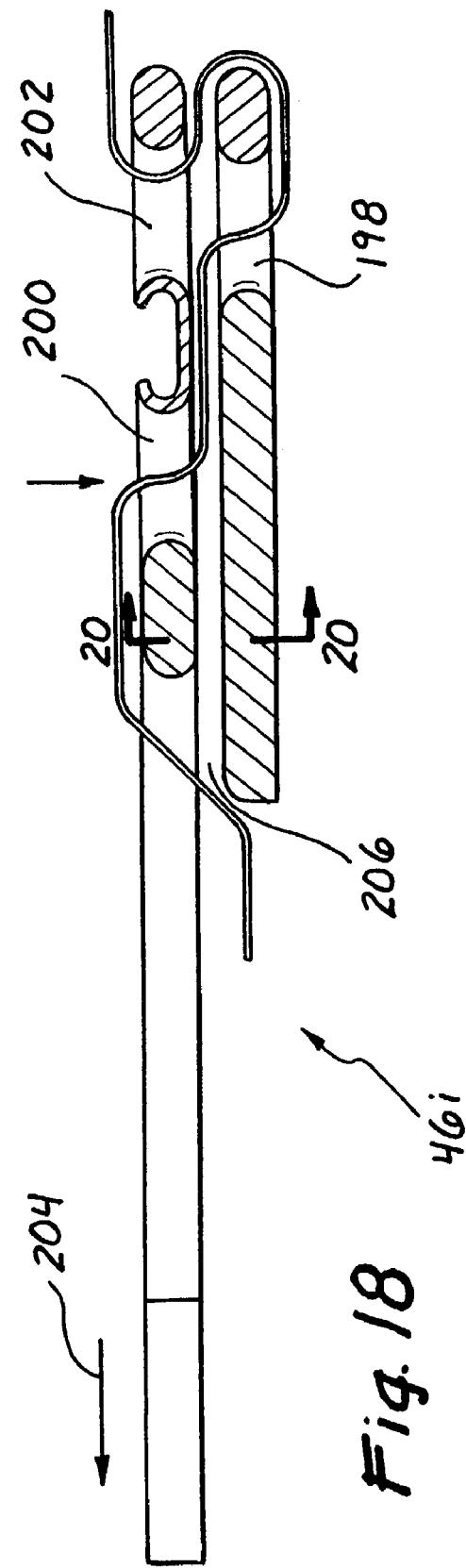
Fig. 17
Fig. 18

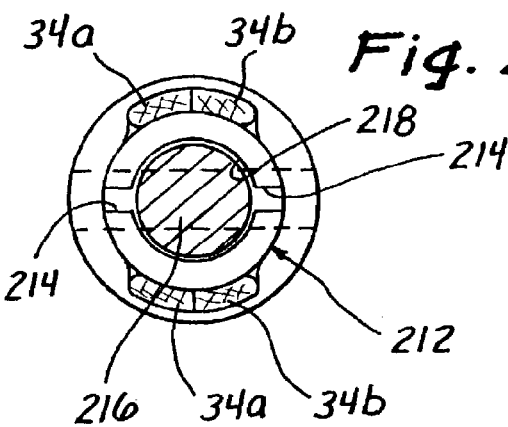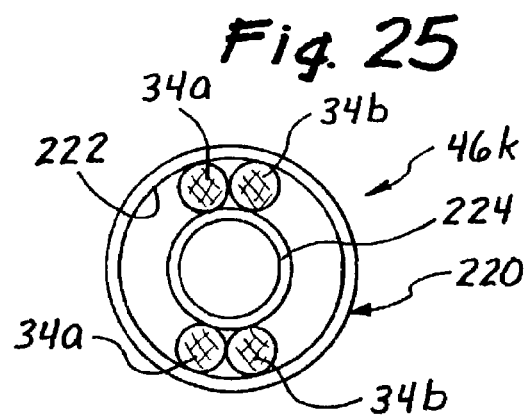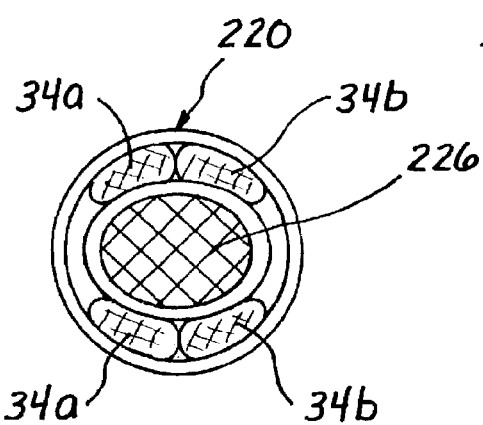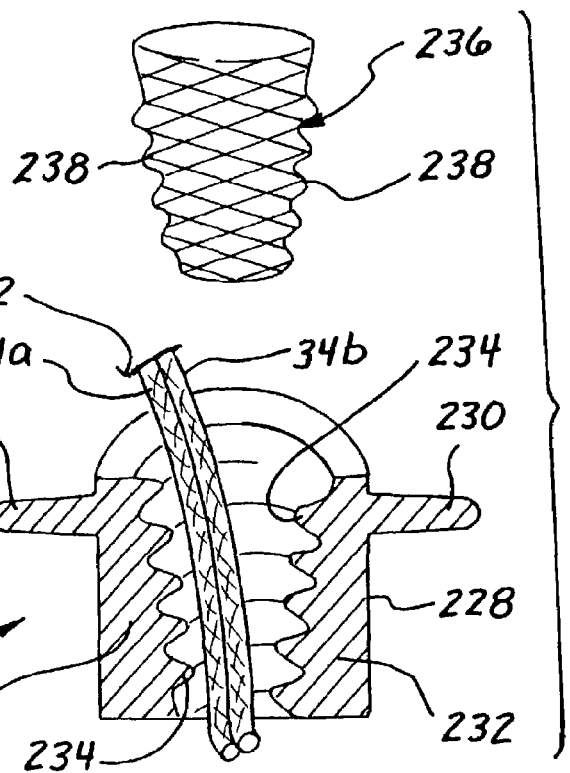

DEVICES AND METHODS FOR REPAIRING SOFT TISSUE

BACKGROUND OF THE INVENTION

The present invention relates to devices and methods for repairing soft tissue, and more particularly to devices and methods for arthroscopic repair of a torn rotator cuff.

It is an increasingly common problem for tendons and other soft, connective tissues to tear or to detach from associated bone. One such type of tear or detachment is a "rotator cuff" tear, wherein the supraspinatus tendon separates from the humerus, causing pain and loss of ability to elevate and externally rotate the arm. Complete separation can occur if the shoulder is subjected to gross trauma, but typically, the tear begins as a small lesion, especially in older patients.

To repair a torn rotator cuff, the typical course today is to do so surgically, through a large incision. This approach is presently taken in almost 99% of rotator cuff repair cases. There are two types of open surgical approaches for repair of the rotator cuff, one known as the "classic open" and the other as the "mini-open". The classic open approach requires a large incision and complete detachment of the deltoid muscle from the acromion to facilitate exposure. The cuff is debrided to ensure suture attachment to viable tissue and to create a reasonable edge approximation. In addition, the humeral head is abraded or notched at the proposed soft tissue to bone reattachment point, as healing is enhanced on a raw bone surface. A series of small diameter holes, referred to as "transosseous tunnels", are "punched" through the bone laterally from the abraded or notched surface to a point on the outside surface of the greater tuberosity, commonly a distance of 2 to 3 cm. Finally, the cuff is sutured and secured to the bone by pulling the suture ends through the transosseous tunnels and tying them together using the bone between two successive tunnels as a bridge, after which the deltoid muscle must be surgically reattached to the acromion. Because of this maneuver, the deltoid requires postoperative protection, thus retarding rehabilitation and possibly resulting in residual weakness. Complete rehabilitation takes approximately 9 to 12 months.

The mini-open technique, which represents the current growing trend and the majority of all surgical repair procedures, differs from the classic approach by gaining access through a smaller incision and splitting rather than detaching the deltoid. Additionally, this procedure is typically performed in conjunction with arthroscopic acromial decompression. Once the deltoid is split, it is retracted to expose the rotator cuff tear. As before, the cuff is debrided, the humeral head is abraded, and the so-called "transosseous tunnels", are "punched" through the bone or suture anchors are inserted. Following the suturing of the rotator cuff to the humeral head, the split deltoid is surgically repaired.

Although the above described surgical techniques are the current standard of care for rotator cuff repair, they are associated with a great deal of patient discomfort and a lengthy recovery time, ranging from at least four months to one year or more. It is the above described manipulation of the deltoid muscle together with the large skin incision that causes the majority of patient discomfort and an increased recovery time.

Less invasive arthroscopic techniques are beginning to be developed in an effort to address the shortcomings of open surgical repair. Working through small trocar portals that minimize disruption of the deltoid muscle, a few surgeons have been able to reattach the rotator cuff using various bone anchor and suture configurations. The rotator cuff is sutured intracorporeally and an anchor is driven into bone at a location appropriate for repair. Rather than thread the suture through transosseous tunnels which are difficult or impossible to create arthroscopically using current techniques, the repair is completed by tying the cuff down against bone using the anchor and suture. Early results of less invasive techniques are encouraging, with a substantial reduction in both patient recovery time and discomfort.

Unfortunately, the skill level required to facilitate an entirely arthroscopic repair of the rotator cuff is inordinately high. Intracorporeal suturing is clumsy and time consuming, and only the simplest stitch patterns can be utilized. Extracorporeal knot tying is somewhat less difficult, but the tightness of the knots is difficult to judge, and the tension cannot later be adjusted. Also, because of the use of bone anchors to provide a suture fixation point in the bone, the knots that secure the soft tissues to the anchor by necessity leave the knot bundle on top of the soft tissues. In the case of rotator cuff repair, this means that the knot bundle is left in the shoulder capsule where it can be felt by the patient postoperatively when the patient exercises the shoulder joint. So, knots tied arthroscopically are difficult to achieve, impossible to adjust, and are located in less than optimal areas of the shoulder. Suture tension is also impossible to measure and adjust once the knot has been fixed. Consequently, because of the technical difficulty of the procedure, presently less than 1% of all rotator cuff procedures is of the arthroscopic type, and is considered investigational in nature.

Another significant difficulty with current arthroscopic rotator cuff repair techniques is shortcomings related to currently available suture anchors. Suture eyelets in bone anchors available today, which like the eye of a needle are threaded with the thread or suture, are small in radius, and can cause the suture to fail at the eyelet when the anchor is placed under high tensile loads.

There are various bone anchor designs available for use by an orthopedic surgeon for attachment of soft tissues to bone. The basic commonality between the designs is that they create an attachment point in the bone for a suture that may then be passed through the soft tissues and tied, thereby immobilizing the soft tissue. This attachment point may be accomplished by different means. Screws are known for creating such attachments, but existing designs suffer from a number of disadvantages, including their tendency to loosen over time, requiring a second procedure to later remove them, and their requirement for a relatively flat attachment geometry.

Another approach is to utilize the difference in density in the cortical bone (the tough, dense outer layer of bone) and the cancellous bone (the less dense, airy and somewhat vascular interior of the bone). There is a clear demarcation between the cortical bone and cancellous bone, where the cortical bone presents a kind of hard shell over the less dense cancellous bone. The aspect ratio of the anchor is such that it typically has a longer axis and a shorter axis and usually is pre-threaded with a suture. These designs use a hole in the cortical bone through which an anchor is inserted. The hole is drilled such that the shorter axis of the anchor will fit through the diameter of the hole, with the longer axis of the anchor being parallel to the axis of the drilled hole. After deployment in to the cancellous bone, the anchor is rotated $90^B$ so that the long axis is aligned perpendicularly to the axis of the hole. The suture is pulled, and the anchor is seated up against the inside surface of the cortical layer of bone. Due to the mismatch in the dimensions of the long axis of the anchor and the hole diameter, the anchor cannot be retracted proximally from the hole, thus providing resistance to pullout. These anchors still suffer from the aforementioned problem of eyelet design that stresses the sutures.

Still other prior art approaches have attempted to use a "pop rivet" approach. This type of design requires a hole in the cortical bone into which a split shaft is inserted. The split shaft is hollow, and has a tapered plug leading into its inner lumen. The tapered plug is extended out through the top of the shaft, and when the plug is retracted into the inner lumen, the tapered portion causes the split shaft to be flared outwardly, ostensibly locking the device into the bone.

Other methods of securing soft tissue to bone are known in the prior art, but are not presently considered to be feasible for shoulder repair procedures, because of physicians' reluctance to leave anything but a suture in the capsule area of the shoulder. The reason for this is that staples, tacks, and the like could possibly fall out and cause injury during movement. As a result of this constraint, the attachment point often must be located at a less than ideal position. Also, the tacks or staples require a substantial hole in the soft tissue, and make it difficult for the surgeon to precisely locate the soft tissue relative to the bone.

As previously discussed, any of the anchor points for sutures mentioned above require that a length of suture be passed through an eyelet fashioned in the anchor and then looped through the soft tissues and tied down to complete the securement. Much skill is required, however, to both place the sutures in the soft tissues, and to tie knots while working through a trocar under endoscopic visualization.

What is needed, therefore, are new approaches for repairing the rotator cuff or fixing other soft tissues to bone, wherein both the bone and suture anchors reside completely below the cortical bone surface, there is no requirement for the surgeon to tie a knot to attach the suture to the bone anchor, and wherein suture tension can be adjusted and possibly measured. The procedures associated with the new approaches should be better for the patient than existing procedures, should save time, be uncomplicated to use, and be easily taught to practitioners having skill in the art.

SUMMARY OF THE INVENTION

Accordingly, the inventors have developed new and novel approaches for securing soft tissue to bone, and particularly for axially anchoring suture which attaches the soft tissue to adjacent bone structure.

More particularly, in one aspect of the invention there is disclosed a suture anchoring device, comprising an anchor housing having an outer wall, a compressible plug member disposed within the housing and extending proximally of the housing, and a channel extending through the plug member for accommodating a length of suture. A cap member is provided for enclosing a proximal end of the housing. In operation, the compressible plug member is compressed in order to anchor the length of suture when the cap member is engaged with the housing.

In another aspect of the invention, there is disclosed a suture anchoring device which comprises an anchor body having an interior threaded wall, as well as a suture return member associated with the body, such as a pin, for returning a distally extending length of suture in a proximal direction. A length of fiber is provided, having a first end secured to a distal portion of the body, and a second end extending from an end of the body, the fiber being wrapped about the interior threaded wall of the body a plurality of times. In operation, when the length of fiber is pulled in a predetermined direction, the wrapped fiber becomes tightly engaged about the suture to anchor the suture.

In yet another aspect of the invention, there is provided a suture anchoring device, which comprises an anchor body having an outer wall, and a suture return member disposed at a distal end of the anchor body, for receiving a length of suture extending distally through the body, and returning a portion of the suture length in a proximal direction. A passage extends along an interior surface of the wall for accommodating the length of suture. The passage tapers in width in a proximal direction, for the purpose of permitting the suture to be moved axially when pulled in a first direction, for approximating a portion of soft tissue to which the suture was attached to adjacent bone, and anchoring the suture axially in place when the suture is pulled in an opposing direction.

In still another aspect of the invention, there is provided a suture anchoring device, comprising an anchor body having an outer wall, as well as a lumen for accommodating a length of suture within the outer wall. A plurality of members are disposed within the anchor body for contacting the length of suture and creating a tortuous path therefor, in order to anchor the length of suture in place. The device further comprises a member radially extending from the body for anchoring the device in adjacent bone.

In another aspect of the invention, there is provided a suture anchoring device, which comprises an axially extending spring, as well as a suture return member or pin disposed distally of said spring. A length of suture extends axially within the spring and about the suture return member. An actuator is disposed at a proximal end of the device for actuating the spring to a compressed state wherein the suture becomes clamped within the spring.

In yet another aspect of the invention, there is provided a suture anchoring device, which comprises a suture return member and a length of suture extending axially through the device about the suture return member. A plurality of axially stacked, spaced plates, comprising leaf springs, are disposed proximally of the suture return member. The aforementioned length of suture extends through apertures in each of the plates. A mandrel is provided for moving the plurality of stacked plates between a first generally planar orientation, wherein the suture is free to move axially therethrough, and a second folded orientation, wherein the suture is axially clamped within the apertures.

In still another aspect of the invention, there is provided a suture anchoring device, which comprises a body, a core disposed within the body, and a length of suture attached to a piece of soft tissue and extending into the body. A portion of the length of suture is wrapped about the core and attached to a distal end thereof. The core is rotatable to adjustably tension the length of suture, and may be rotationally locked in order to anchor the length of suture in place.

In another aspect of the invention, there is provided a suture anchoring device, which comprises an outer tube, as well as a first plate having a suture receiving aperture disposed therein. A second plate has a suture receiving aperture disposed therein. A connection between the first and second plates is designed to break when a predetermined force is applied thereto. The system is designed so that axial displacement of one of the plates relative to the other of the plates causes application of the predetermined force, to separate the plates, and thus create a tortuous path for a length of suture passing therethrough.

In still another aspect of the invention, there is provided a suture anchoring device. This device comprises an outer tube having a lumen extending axially therethrough, and a length of suture extending distally through the outer tube, about a suture return member, and proximally back through the outer tube. An inner expandable member extends axially through the lumen, between portions of the length of suture, the inner expandable member being actuatable to a radially expanded state in order to compress and clamp the length of suture in place. In one embodiment, the inner expandable member comprises a split elastomeric tube, while in a second embodiment, the inner expandable member comprises a spring coil.

The invention, together with additional features and advantages thereof, may best be understood by reference to the following description taken in conjunction with the accompanying illustrative drawing.

BRIEF DESCRIPTION OF THE DRAWINGS

FIG. 1A is a partial sectional view through the left shoulder of a human as seen from the front showing the use of a minimally invasive soft tissue to bone attachment system, or suture anchor system, of the present invention;

FIG. 1B is an enlarged sectional view taken within the circle denoted 1B in FIG. 1A;

FIGS. 1C–1F are enlarged sectional views of several steps in the use of the suture anchor system of FIG. 1A to reattach a rotator cuff tendon;

FIG. 7 is a perspective view of a jam cleat suture anchoring apparatus, in accordance with still another embodiment of the present invention;

FIG. 8 is a cross-sectional view showing another suture lock embodiment, comprising a multi-lock anchor, prior to deployment;

FIG. 9 is a cross-sectional view of the multi-lock anchor shown in FIG. 8, after it has been deployed to lock the suture;

FIG. 17 is a cross-sectional view of still another suture anchoring device, shown in an undeployed position;

FIG. 18 is a cross-sectional view similar to FIG. 17, illustrating the suture anchoring device after it has been deployed to anchor the suture in place;

FIG. 24 is a cross-sectional view similar to that of FIG. 23, wherein the split tube has been expanded to lock the suture in place;

FIG. 25 is a cross-sectional end view of another suture anchoring embodiment, comprising a cylinder in which is disposed a spring coil and suturing material;

FIG. 26 is a cross-sectional view similar to FIG. 25, wherein the spring coil has been expanded to anchor the suturing material in place; and FIG. 27 is a cross-sectional view of still another suture anchoring embodiment, comprising a binding tapered threaded anchor.

DESCRIPTION OF THE PREFERRED EMBODIMENT

Figure 1F:
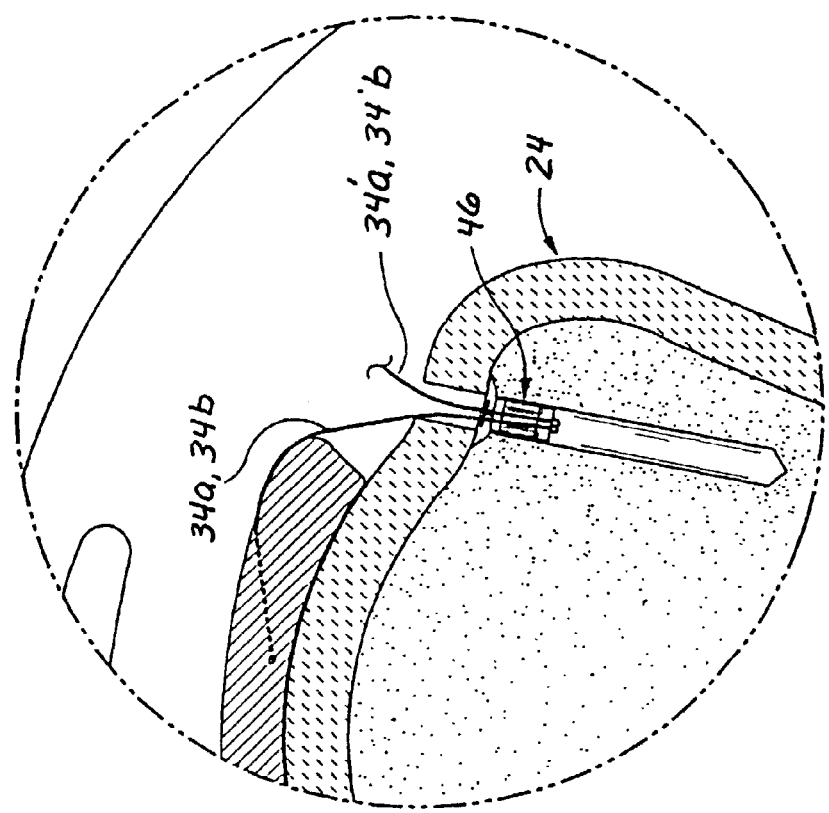

The present invention provides improved knotless suture anchor devices and methods for anchoring a length of suture with respect to a body cavity. In the exemplary embodiments described herein, the inventive devices are used to anchor a length of suture to a bone structure, specifically the humeral bone of the human shoulder. The length of suture is desirably looped through soft tissue, such as a rotator cuff tendon, to approximate and fix the soft tissue with respect to the body cavity (e.g., bone structure). It should be understood, however, that the suture anchor apparatus described herein may be utilized to secure a length of suture to body cavities other than in a bone structure, and may even be used to anchor the suture outside of a body cavity, or merely to a predetermined location within the body. In this regard, the various inventive embodiments include an anchor body within which the length of suture may be anchored without knots. If the anchor body is to be implanted within the body cavity, structure on its exterior or coupled therewith may also be provided for securing the anchor body therein.

As mentioned, the present invention is particularly well-suited for repairing rotator cuff injuries by re-attaching the rotator cuff tendon to the outside of the humeral head. The invention permits minimally invasive surgeries on such injuries and greatly facilitates rapid and secure fixation of the rotator cuff tendon to the humeral head. It should be understood that the same principles described herein apply to the repair of other injuries in which soft tissue is to be re-attached to a bone structure.

FIGS. 1A–1F are cross-sectional views through the left shoulder of a human as viewed from the front and illustrate the use of an exemplary soft tissue to bone attachment system, or suture anchor system 20, for repairing a rotator cuff tendon injury. The rotator cuff tendon 22 is shown in its natural position overlying the bulbous humeral head 24 of the humerus bone 26. In rotator cuff injuries, the tendon 22 partially or completely separates from its attachment point to the humeral head 24, which point of attachment is typically located along an angled shelf, the greater tuberosity 28. In minimally invasive surgeries to repair the rotator cuff injury, the surgeon threads one or more sutures through the rotator cuff tendon 22 and anchors them to the greater tuberosity 28. The suture anchor system 20 of the present invention facilitates this latter step of anchoring the sutures to the greater tuberosity 28.

With reference first to FIG. 1A, a generally tubular trocar 30 provides a conduit through the soft tissue of the shoulder for passage of the suture anchor system 20 of the present invention. Per convention, the trocar has a proximal end outside of the patient that the surgeon manipulates, and a distal probe or end that enters the body and through which the surgery is performed. Typically, the surgeon makes an incision or stab wound through the outer dermal layers of sufficient size to permit passage of the trocar 30 through the skin and the deltoid muscle, into proximity with the humeral head 24. Various trocars and techniques for creating the approach passageway are known and may be utilized with the present invention. In addition, more than one incision and conduit may be necessary to perform the several suturing and anchoring steps.

After establishing one or more direct conduits to the humeral head 24, the surgeon passes a length of suture through the soft tissue of the rotator cuff tendon 22 so that a loop 32 of suture material is embedded therein, as seen in FIG. 1B. The two free ends 34a, 34b of the length of suture are withdrawn from the patient and coupled to the suture anchor system 20. The specifics of this coupling and subsequent manipulation of the two free ends of the suture will be described more fully below, in conjunction with each of the described embodiments. For the purpose of explaining the exemplary method of use, it is sufficient to understand that the two free ends 34a, 34b pass through or about the suture anchor system 20. Therefore, the two free ends 34a, 34b are shown at the top of FIG. 1B projecting from a proximal end of the system 20.

The exemplary suture anchor system 20 as illustrated is particularly suitable for anchoring a suture to a body cavity, specifically the humeral head 24 as shown. When anchoring sutures to such a bone structure, a conventional technique is to first form a blind hole or cavity 40 through the cortical layer 42 and into the soft cancellous matter 44, as seen in FIGS. 1B and 1C. The surgeon then positions a suture anchor 46 within the cavity 40 and secures it therein to prevent removal from the cavity.

The suture anchor 46 performs two functions: anchoring itself within the body cavity and anchoring the sutures therein. In the embodiment as illustrated in FIGS. 1C and 1D, the former function is accomplished using an expandable anchoring member 48 located at the proximal end of the suture anchor 46. The anchoring member 48 functions like a toggle bolt used in ceiling fixtures, and specifically expands to a larger dimension in the cavity 40 beyond the hard cortical bone 42. FIG. 1D shows the anchoring member 48 after having been radially expanded from proximal movement of the suture anchor 46 (compare to the axial location of the suture anchor in FIG. 1C). In this manner, the suture anchor 46 is prevented from being removed from the cavity 40 once the anchoring member 48 is deployed.

The present invention illustrates a particular anchoring member 48, although any similar expedient will work. For example, a different toggle-like anchoring member may be used such as shown in co-pending application Ser. No. 09/876,488 filed on Mar. 2, 2001, expressly incorporated by reference herein. Alternatively, an anchoring structure that expands into contact with the cancellous matter 44 or a body resembling a screw may also be used. In short, the present invention is not considered to be limited by the particular anchoring structure that secures the suture locking portion to the bone or other body cavity.

The second function of the suture anchor 46 is the anchoring or fixation of the suture with respect to the suture anchor itself, without the use of knots. Desirably, the particular manner of anchoring the suture with respect to the suture anchor 46 permits easy adjustment of the length of suture between the suture anchor 46 and the loop 32 formed in the soft tissue prior to anchoring the suture. This adjustment allows the surgeon to establish the proper tension in the length of suture for effective repair of the soft tissue, and reattachment of the rotator cuff tendon 22 in the illustrated embodiment. So, for example, FIG. 1D also illustrates the two free ends 34a, 34b of the length of suture having been pulled taught prior to securing within the suture anchor 46 (see comparison with FIG. 1C).

Figure 1E:
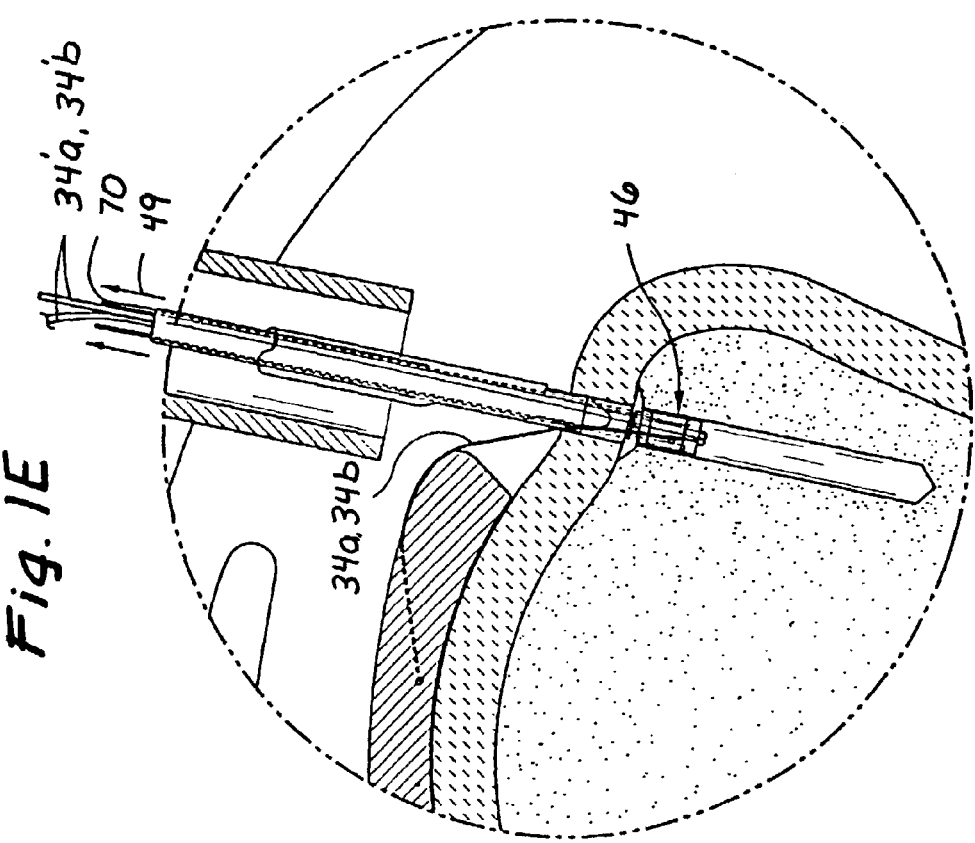

FIG. 1E shows the fully deployed suture anchor 46 after the free ends 34a, 34b have been placed in tension and locked within the suture anchor, in various manners to be described below in connection with the descriptions of each of the several disclosed embodiments.

Although not shown, the remaining steps in the procedure involve withdrawing portions of the suture anchor from the surgical site as seen in FIG. 1F and severing the free ends 34a', 34b' close to the suture anchor 46. It should be noted that no portion of the suture anchor 46 or sutures 34a', 34b' projects above the outer surface of the humeral head 24, and in addition no knots are left to irritate the patient.

Although the present invention is described primarily in conjunction with the repair of a torn rotator cuff, the apparatus and method could also be used in arthroscopic repair at other sites, such as the knee, elbow, or hip, for example, as well as in conjunction with other surgical techniques, such as traditional open or mini-open surgical procedures.

Figure 2:
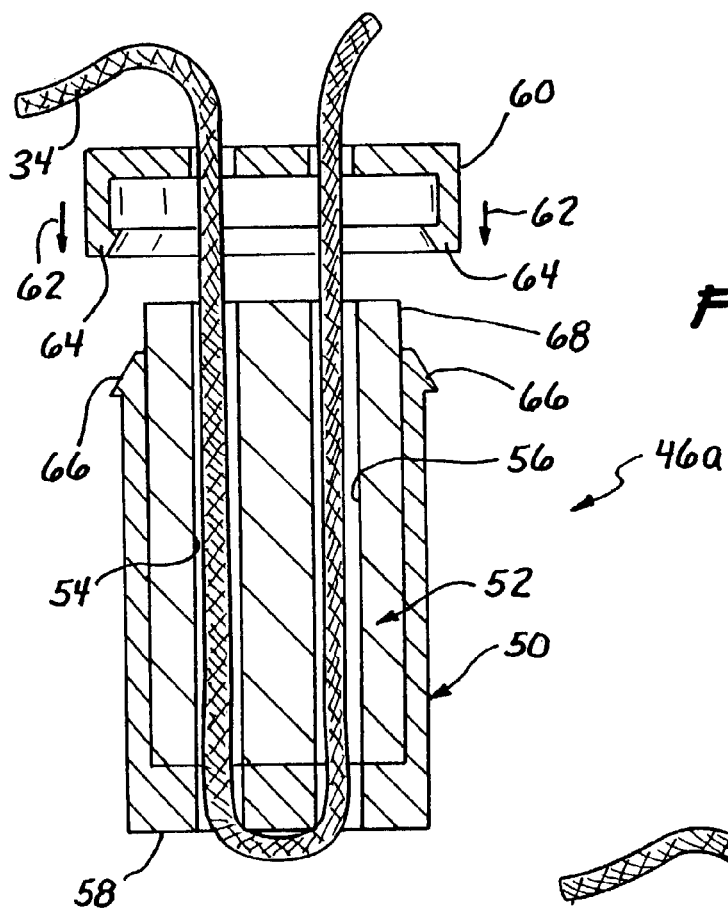
FIG. 2 is a cross-sectional view of a suture anchor comprising a compliant plug, in accordance with one embodiment of the present invention, wherein the suturing material is not secured in place.
Figure 3:
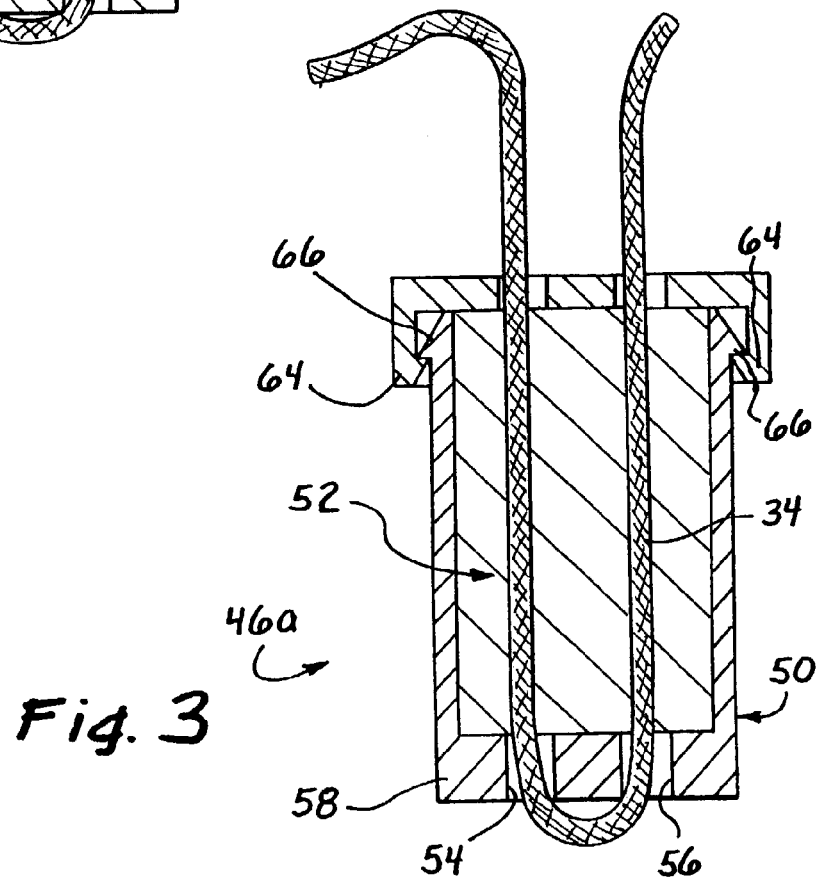
FIG. 3 is a cross-sectional view similar to FIG. 2, wherein the cap is secured to the housing of the suture anchor in order to secure the suturing material in place.

Now with reference to FIGS. 2 and 3, there is shown a first embodiment of the present invention. In this embodiment, a suture anchor 46a comprises a rigid outer housing 50, which may be fabricated of any suitable rigid biocompatible material. It should be noted that the usage of the reference numeral 46a is intended to convey that the inventive embodiment is usable in the procedure discussed in connection with FIGS 1A–1F, in place of the suture anchor 46 disclosed therein, which is illustrative only. Within the housing 50 is a compliant plug 52, comprised of a suitable elastomeric material. Channels 54 and 56 extend axially through the plug 52 and a lower housing portion 58, for accommodating a length of suture 34 extending therethrough, as shown. The suture anchor 46a further comprises a rigid cap 60, which is engageable with an upper portion of the housing 50.

In operation, as shown in FIG. 2, the cap 60 is initially separated from the housing 50, to permit the length of suture 34 to be disposed through the channels 54, 56, as shown. When the cap 60 is disengaged from the housing 50, the suture length 34 is freely movable through the housing 50, by applying a tensile force to one end or the other of the suture length, in order to tension the suture and approximate the soft tissue 22 (FIGS. 1A–1F) to the bone 24, as desired. Once the attachment procedure described in connection with FIGS. 1A–1F has been completed, and the soft tissue 22 is satisfactorily in place relative to the bone 24, the cap 60 is engaged with the housing 50 of the compliant plug suture anchor 46, by moving it in the direction of the arrows 62 until lower engaging portions 64 of the cap 60 and upper engaging portions 66 may be snap-fitted together, as shown in FIG. 3, or otherwise connected in ways well known in the art, such as a threaded fitting or other suitable means. The purpose of this step is to anchor the suture in place, as illustrated in FIGS. 1E. Because there is excess plug material within the housing 50, with a portion 68 extending above the upper engaging portions 66 of the housing 50, as shown in FIG. 2, the placement of the cap 60 on the housing 50 causes the compliant plug material 52 to be significantly compressed within the housing 50, such that the channels 54, 56 are also compressed, thereby clamping or locking the suture in place, so that it is no longer slidable through the channels 54 and 56.

Figure 4:
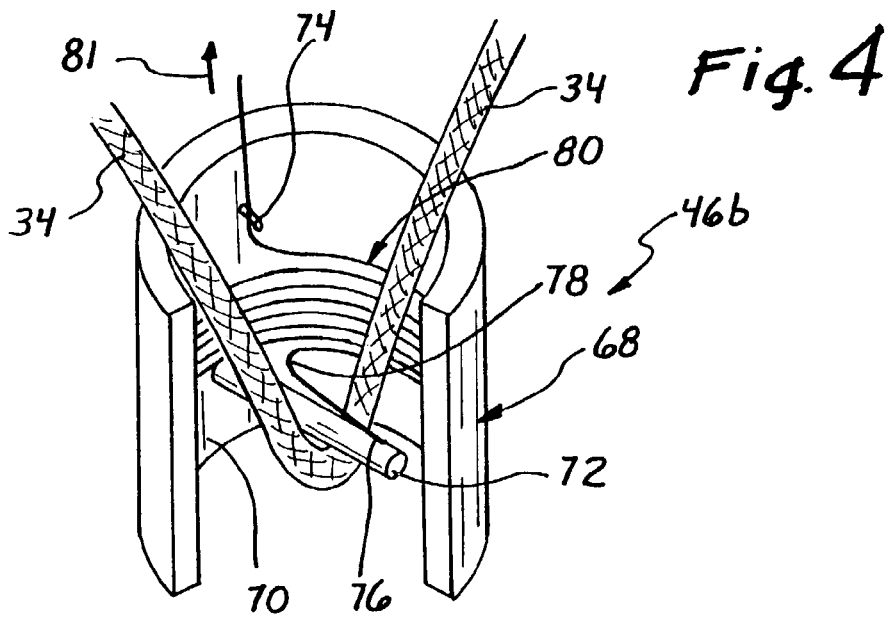
FIG. 4 is a perspective view of a suture anchor comprising a drum spinning apparatus, in accordance with another embodiment of the present invention, wherein the suturing material is not yet secured in place.
Figure 5:
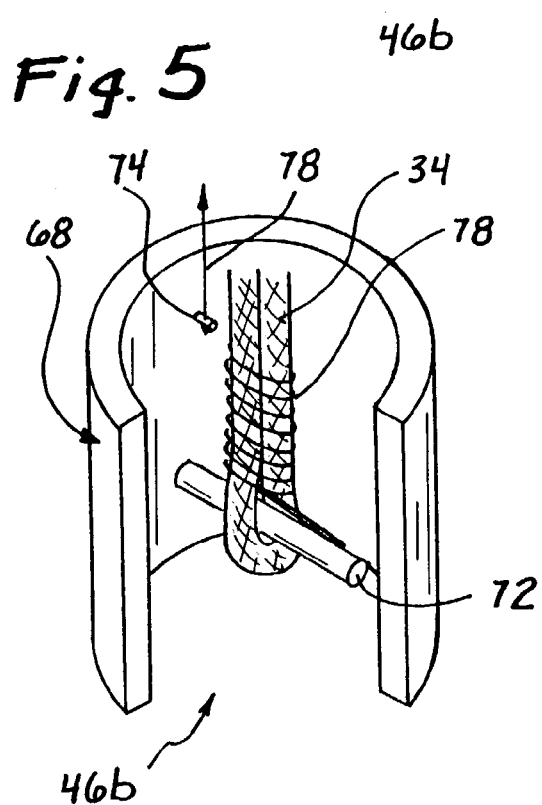
FIG. 5 is a perspective view similar to FIG. 4, wherein the suturing material is secured in place.

Now with reference to FIGS. 4 and 5, there is shown an alternative suture anchoring device 46b, which comprises a cylindrical insert or body 68 having an interior wall 70, which may be threaded, as shown. The insert 68 is adapted for disposition within the blind hole or cavity 40 (FIG. 1D). A suture return member or primary pin 72 is disposed across the inner diameter of the insert 68, and may be suitably secured to the interior wall 70 in either a rotatable or fixed fashion, as desired. A secondary pin 74 protrudes from the interior wall 70 at a location above the primary pin 72. One end 76 of a length of monofilament fiber 78 is secured to the primary pin 72, and a second end thereof is disposed about the secondary pin 74 and extends upwardly out of a proximal end of the insert 68. The majority of the length of monofilament fiber 78 forms a drum 80 which is threadedly engaged with the interior wall 70, as illustrated in FIG. 4.

In operation, the suture length 34 is disposed in the insert 68, from a proximal direction, and wrapped around the primary pin 72, as shown in FIG. 4. The soft tissue 22 is approximated to the bone 24, as described in connection with FIGS. 1A–1F, by tensioning the suture 34 such that it moves axially about the primary pin 72. When this process is completed, and it is desired to lock the suture in place, the length of monofilament fiber 78 is pulled proximally, in the direction of arrow 81, thereby causing the drum 80 of monofilament fiber to spin circumferentially. The result of this process is that the monofilament fiber 78 becomes tightly wrapped about the suture 34, with multiple loops, as shown in FIG. 5, thus locking the suture 34 in place lengthwise.

FIG. 7 illustrates still another suture anchor 46c which may be identified as a "jam cleat" or "boat cleat"—type mechanism. More particularly, the anchor 46c comprises a generally cylindrical body portion 82, which preferably includes threads 84 on at least a portion of its outer surface for engaging adjacent bone within the blind hole or cavity 40 (FIG. 1B). A pin 86 is disposed across the internal diameter of the body portion 82, in a manner similar to the pin 72 in FIGS. 4 and 5, secured at each end to the inner cylindrical wall 88 in either a fixed or rotatable manner. In use, the suture 34 extends axially through the cylinder 84 and about the pin 86, with a first end being attached to the soft tissue 22 (FIGS. 1A–1F) in the direction of arrow 90, and the second end extending proximally out of the patient's body through an access cannula (not shown). The portion of the suture length 34 which extends between the pin 86 and the soft tissue extends through a cleat portion 92, which comprises a "V" shaped passage 94 that progressively narrows in a proximal direction, as well as a plurality of ribs 96. This suture anchoring system operates in a manner similar to that of a boat cleat, in that the suture 34 may be pulled proximally through the cannula to tension the soft tissue against the bone, as desired. The V-shaped passage 94 permits movement of the suture in this direction, in order to provide the practitioner performing the procedure with the ability to selectively tension the soft tissue. However, because of the progressively narrowing passage diameter in the opposing direction, the suture cannot be moved in the direction of the arrow 90, thus effectively locking the suture in place, as well as the soft tissue 22.

Figure 6:
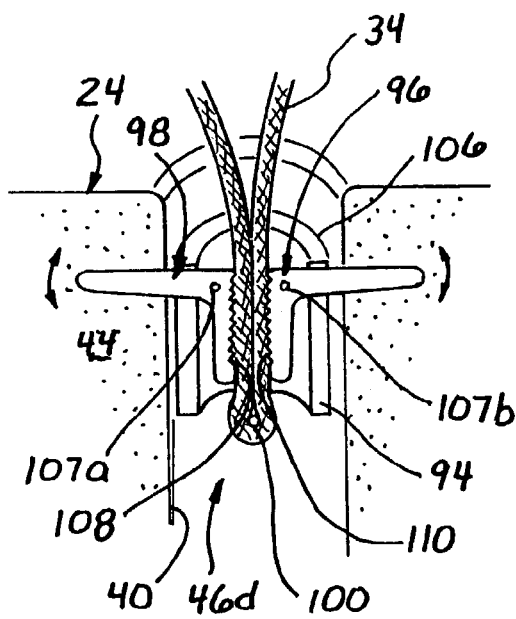
FIG. 6 is a cross-sectional view illustrating a cam cleat suture anchoring apparatus, in accordance with yet another embodiment of the present invention.

Now with reference to FIG. 6, there is shown yet another modified embodiment of a suture anchor 46d, which comprises, once again, a generally cylindrical anchor body 94, within which are disposed a pair of cam cleats 96, 98. A pin 100 is disposed within the cylindrical body 94 as well, in the same manner as is the case for pin 86 in the embodiment of FIG. 7. The suture length 34 extends distally through the cylindrical body 94, is wrapped about the pin 100, which functions as a suture return member, and is returned proximally through the cannula (not shown). The first end 102 of the suture 34 is attached to the soft tissue to be repaired, while the second end 104 is available for the practitioner to use in tensioning the suture, by applying tension proximally thereon. A body cap portion 106 is disposed above the main body portion 94. The cam cleats 96, 98 are pivotally attached to the main body portion or housing 94 by means of pivot pins 107a, 107b, respectively. In operation, once the cylindrical body portion 94 is in position within the bone cavity 40, below the cortical bone layer, the device is pushed down to release the cleats 96, 98 so that they pivot about the pivot pins 107a, 107b. This action separates the cleats 96, 98 sufficiently to permit the suture to be tightened to tension the soft tissue, by pulling proximally on the second suture end 104. Tension on the suture 34 creates a force which attempts to pull the anchor out of the bone cavity 40. This force creates a moment on the cleats 96, 98, which increases the radially outward pivoting thereof described above, thus extending them substantially into the cancellous bone matter 44, as shown in FIG. 6, so that the device 46d becomes anchored within the bone. Subsequently, once the soft tissue has been properly positioned and suitably tensioned, the body 94 is permitted to float upwardly in a proximal direction, thereby pushing the interior toothed surfaces 108, 110 of each respective cleat 96, 98 together and locking the suture 34 in place.

A somewhat similar embodiment to that of FIG. 6 is illustrated in FIGS. 8 and 9. This embodiment 46e includes a generally cylindrical body 112. Two suture free ends 34a, 34b extend axially through a lumen 114 of the body 112. The body 112 comprises an outer cylinder 116 having bone lock apertures 118 and 120, and an inner member 122 comprising internal bone lock members 124, 126, together with designed points of weakness 128 and 130. In FIG. 8, the device 46e is shown in an undeployed state.

FIG. 9 illustrates the device 46e in a deployed condition. Deployment is initiated, in a preferred method, by actuating a mandrel 132 in a distal direction, as shown by arrows 134, until the mandrel 132 engages external lock edges 136, 138 on the outer cylindrical body 116, thereby moving the outer cylinder 116 in a distal direction as well. At the same time, the inner member 122 is pulled in a proximal direction, as shown by arrows 140. The distal movement of outer cylinder 116, in combination with the proximal movement of inner member 122, causes contact of the internal bone lock members 124, 126 with portions of the outer cylinder 116 which define the proximal edges of apertures 118, 120, respectively, thereby causing the bone lock members 124, 126 to be pushed radially outwardly so that their ends are engaged with adjacent cancellous bone 44', as shown in FIG. 9. Thus, the device 46e is now locked (anchored) axially in the bone and prevented from proximal movement.

Once the bone lock feature has been deployed, a predetermined applied tensile force proximally on the inner member 122 will cause separation of a proximal portion 142 from the remaining portion of the inner member 122 at the designed point of weakness 128, as shown in FIG. 9. At this juncture, an inner member locking portion 144, which has an increased width relative to the width of remaining portions of the inner member 122, has moved proximally along an axis of the device 46e sufficiently to be co-incident with the aperture 120. Consequently, a portion of the locking portion 144 is caused to slip radially outwardly into the aperture 120, as shown, in order to axially lock the inner member relative to the outer member. The forces involved in deploying the bone lock members 124 and 126 also function to compress the distal end of the outer wall of the inner member 122, causing the locking portion 144, and a bulbous portion 146 on an opposing side of the inner member 122, which is axially offset from the locking portion 144, to overlap one another, as shown in FIG. 9, thus creating a tortuous path 148 for the suture 34. This tortuous path functions as a suture lock, preventing the suture 34 from moving axially within the device 46e.

Figure 10:
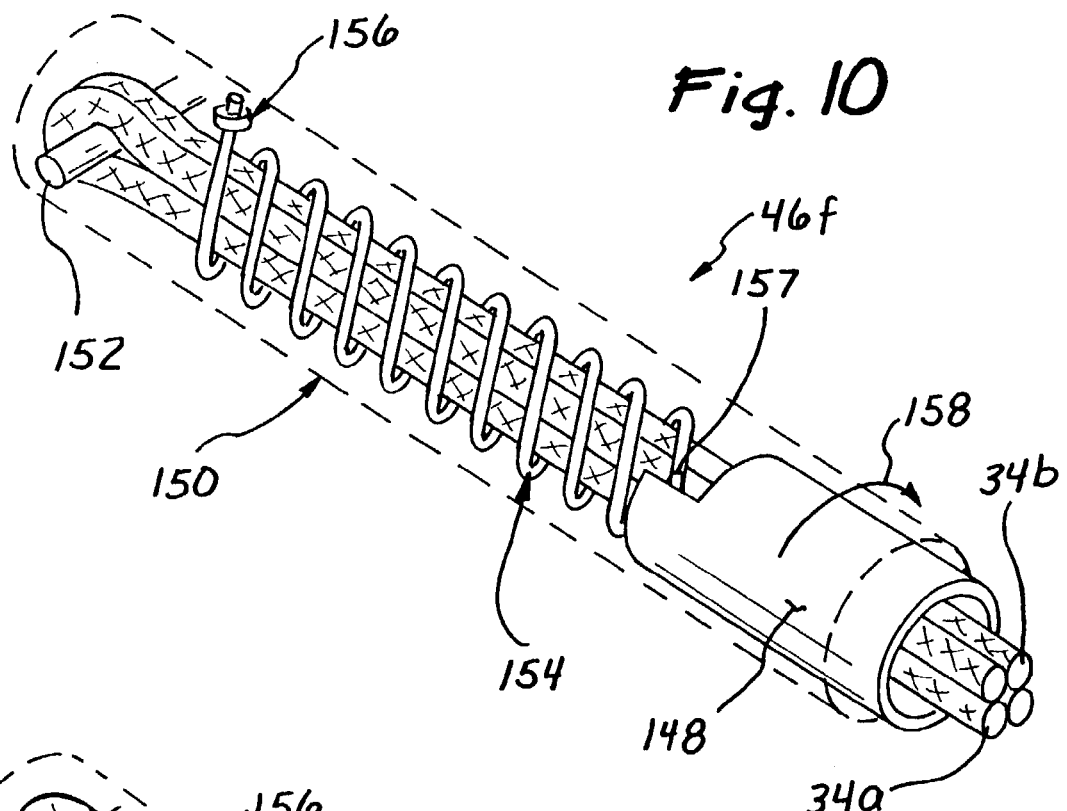
FIG. 10 is a perspective view of a spring-locking suture anchor embodiment, wherein it has not yet been deployed to anchor the suture in place.
Figure 11:
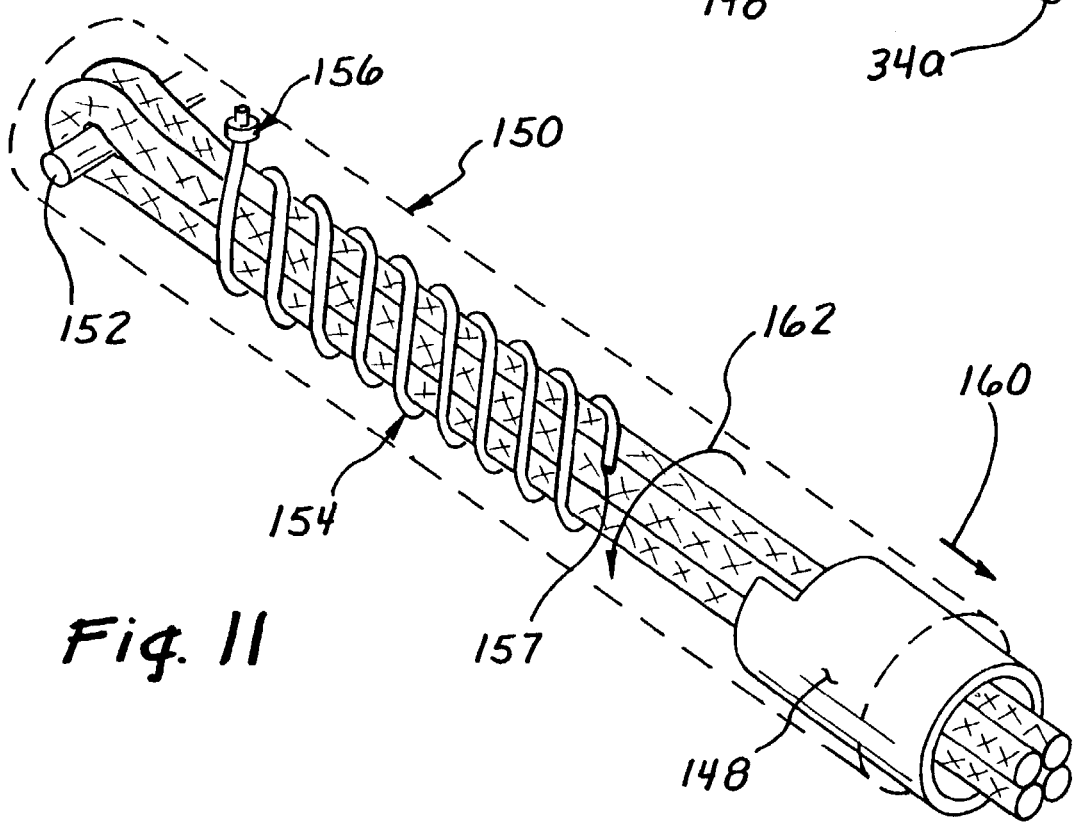
FIG. 11 is a perspective view of the spring-locking suture anchor embodiment of FIG. 10, showing the anchor is a deployed orientation.

Yet another suture anchoring device 46f, which may be called a "spring-lock" anchor, is illustrated in FIGS. 10 and 11. In FIG. 10, the device 46e is shown in an undeployed state, and comprises a driver 148 disposed within an anchor body 150. A suture return pin 152 is disposed within the body 150, in either a fixed or rotatable fashion, as has been discussed in connection with previously described embodiments, about which lengths of suture 34a and 34b are disposed, as shown. The suture lengths 34a and 34b are threaded through a spring 154, one end of which is secured to the anchor body at an anchor point 156. The wire forming the spring 154 can be of a number of different shapes, including round, square, hexagonal, rectangular, and the like. A free end 157 of the spring 154 abuts a distal portion of the driver 148, as shown. In operation, when it is desired to tension the suture 34, thus also approximating the soft tissue 22 to the bone 24 (FIGS. 1A–1F), the driver 148 is rotated in a clockwise direction, as shown by arrow 158. This action causes the free end 157 of the spring to move in a clockwise direction as well, thus expanding the inside diameter of the spring 154, thereby permitting axial movement of the suture 34a, 34b as desired.

Then, when it is desired to anchor the suture in place, the driver 148 is retracted proximally, in the direction of arrow 160, as shown in FIG. 11. This causes the spring to want to relax to its normal state, thus moving in a counter-clockwise direction as shown by arrow 162. As a result, the spring 154 wraps itself about the suture lengths 34a, 34b to compress and lock them in place within the spring.

Not illustrated, but contemplated within the scope of the invention, is the inclusion of a compressible sleeve around which the spring 154 may be wrapped, and through which the suture 34 may be threaded. When the spring collapses, the sleeve also collapses on the suture, thereby locking it in place.

Figure 12:
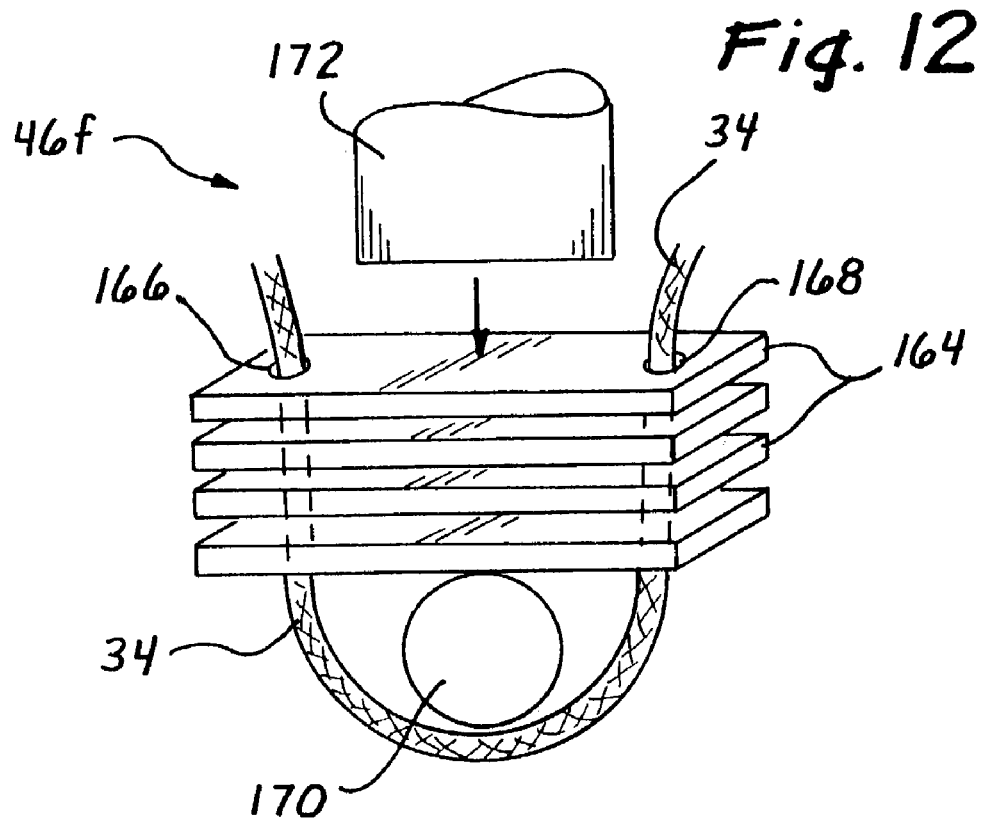
FIG. 12 is a front perspective view of yet another suture lock embodiment, comprising a plurality of leaf springs in an undeployed state.
Figure 13:
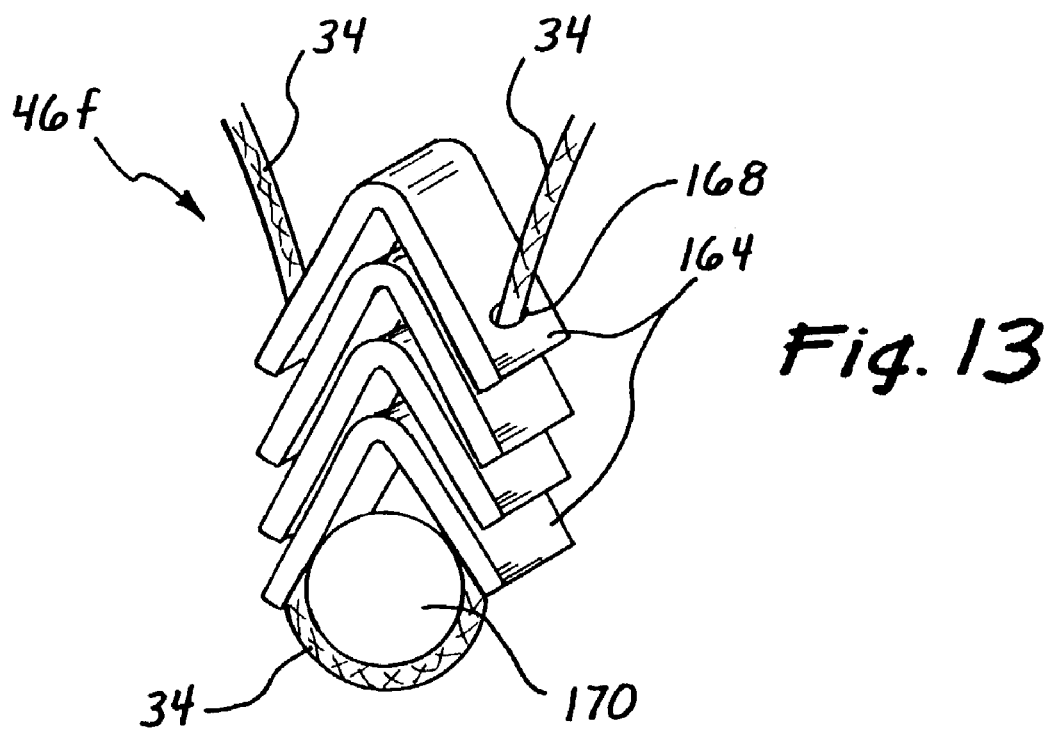
FIG. 13 is a view similar to FIG. 12, showing the springs in a deployed state for locking the suture.

Now, with reference to FIGS. 12 and 13, there is shown still another suture anchor embodiment, wherein a plurality of stacked leaf springs 164 are employed to lock a suture length 34 in place. The leaf springs 164 may be made of any biocompatible material, including stainless steel, absorbable or non-absorbable plastic materials, and the like. In FIG. 12, the device 46f is shown in an undeployed state, the leaf springs 164 being in a flat, stacked, axially spaced configuration. Each spring 164 includes a pair of apertures 166, 168, for accommodating the suture 34 therethrough. The suture length 34 extends distally through the first set of apertures 166, about a suture return pin 170, then proximally through the second set of apertures 168. A mandrel 172 is pressed distally against the proximal-most leaf spring 164 to maintain the leaf springs 164 in the aforementioned flat configuration, which is also the deformed state for the leaf springs. In this deformed configuration, the suture 34 may be freely threaded through the apertures 166, 168 of each leaf spring 164, and tensioned as desired to approximate the soft tissue 22 to the bone 24.

When the tensioning step has been completed as desired, the mandrel 172 is 20 withdrawn proximally, thereby releasing the leaf springs 164, so that they may return to their undeformed state, as shown in FIG. 13. In this configuration, the suture 34 is trapped and bound within the apertures 166 and 168, which have now assumed an elliptical shape, and about the pin 170, thus functioning as a suture anchor.

Figure 14:
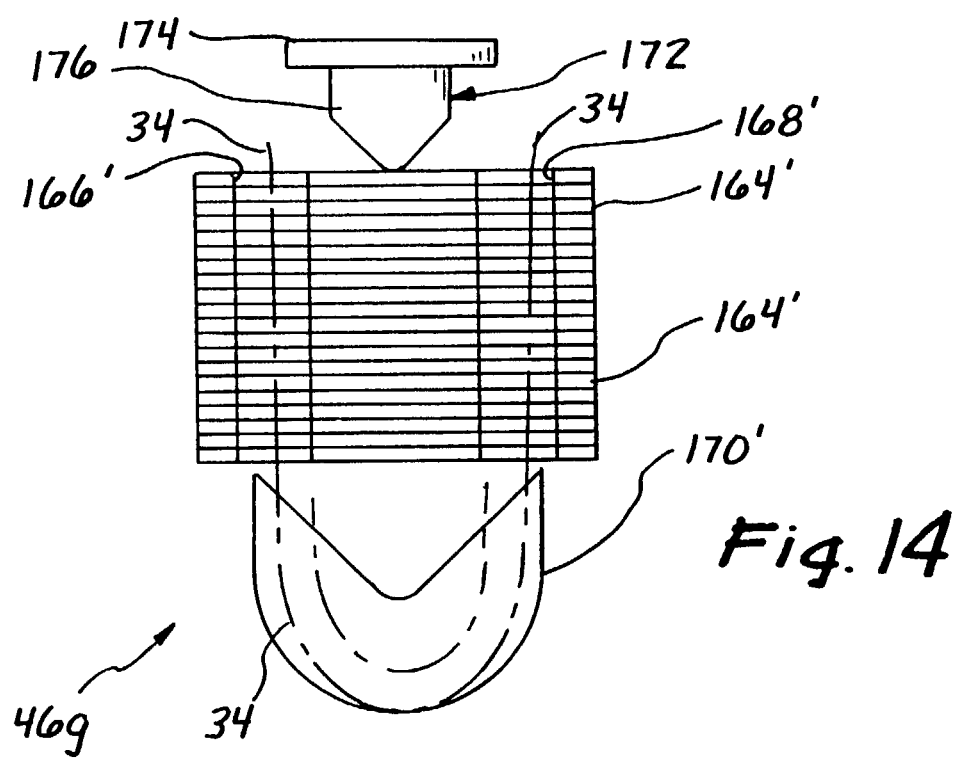
FIG. 14 is a front view of a modified leaf spring suture locking system, shown in an undeployed state.
Figure 15:
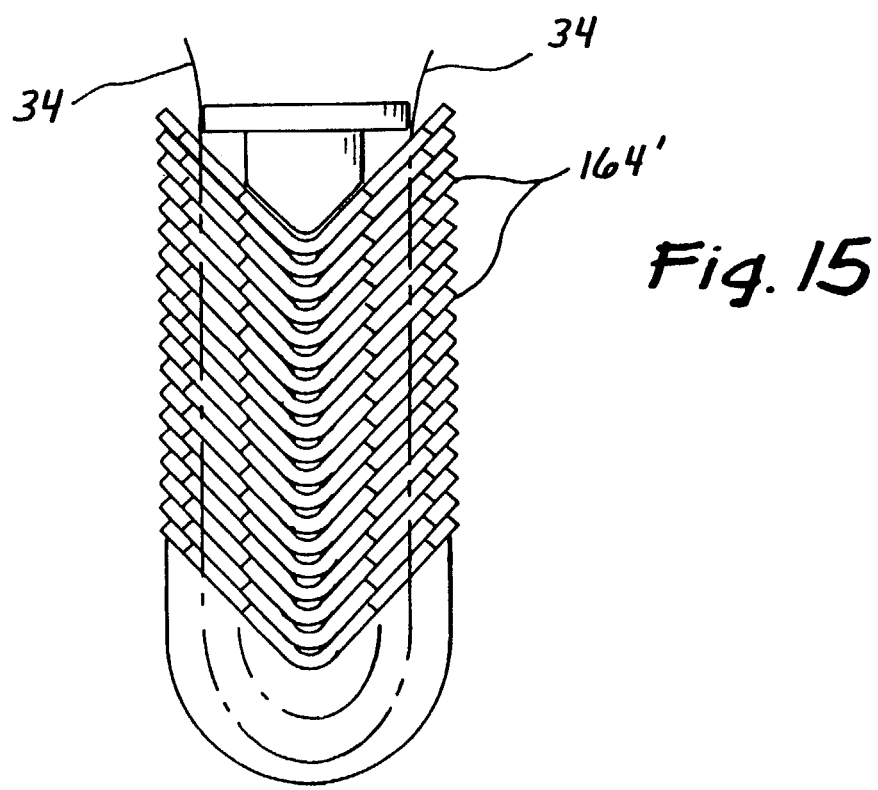
FIG. 15 is a front view similar to FIG. 14, wherein the leaf springs have been deployed to lock the suture in place.

In FIGS. 14 and 15, there is shown another embodiment of a suture anchor 46g, which is similar in many respects to the embodiment of FIGS. 12 and 13. FIG. 14 illustrates the suture anchor in an undeployed state, comprising a length of suture 34 which extends both distally and proximally through a stack of leaf springs 164', in a manner similar to the embodiment of FIGS. 12 and 13, as well as about a suture return member 170'. A major difference between this embodiment, and the embodiment of FIGS. 12 and 13, is that in this embodiment the leaf springs 164' are undeformed in their flat state, as shown in FIG. 12. The materials from which leaf springs 164' may be manufactured are similar to those from which the leaf springs 164 in the embodiment of FIGS. 12 and 13 may be manufactured. The device 46g is inserted into the bone cavity 40 (not shown in FIGS. 14 and 15) sufficiently distally such that the mandrel 172' is disposed beneath the cortical bone 42. The proximal cap portion 174 of the mandrel 172' is rotated to extend beyond the width of the cavity 40, and thus anchor the stack of leaf springs 164' axially beneath the cortical bone layer. The soft tissue 22 is then approximated to the adjacent bone 24 by tensioning the suture 34 as desired, since it is freely movable through the leaf spring stack in the undeployed state. Then, as shown in FIG. 15, when the tensioning step is completed, the mandrel 172' is moved distally, relative to the suture return member 170', by pulling a wire running through the stack of leaf springs 164' or other suitable method. A distal portion 176 of the mandrel 172' comprises a wedge shape which impacts the leaf springs 164', causing them to deform into the folded configuration shown in FIG. 15. This folding action causes a reduction in cross-section of the apertures 166', 168' through which the suture length 34 extends, thereby locking the suture in place.

Figure 16:
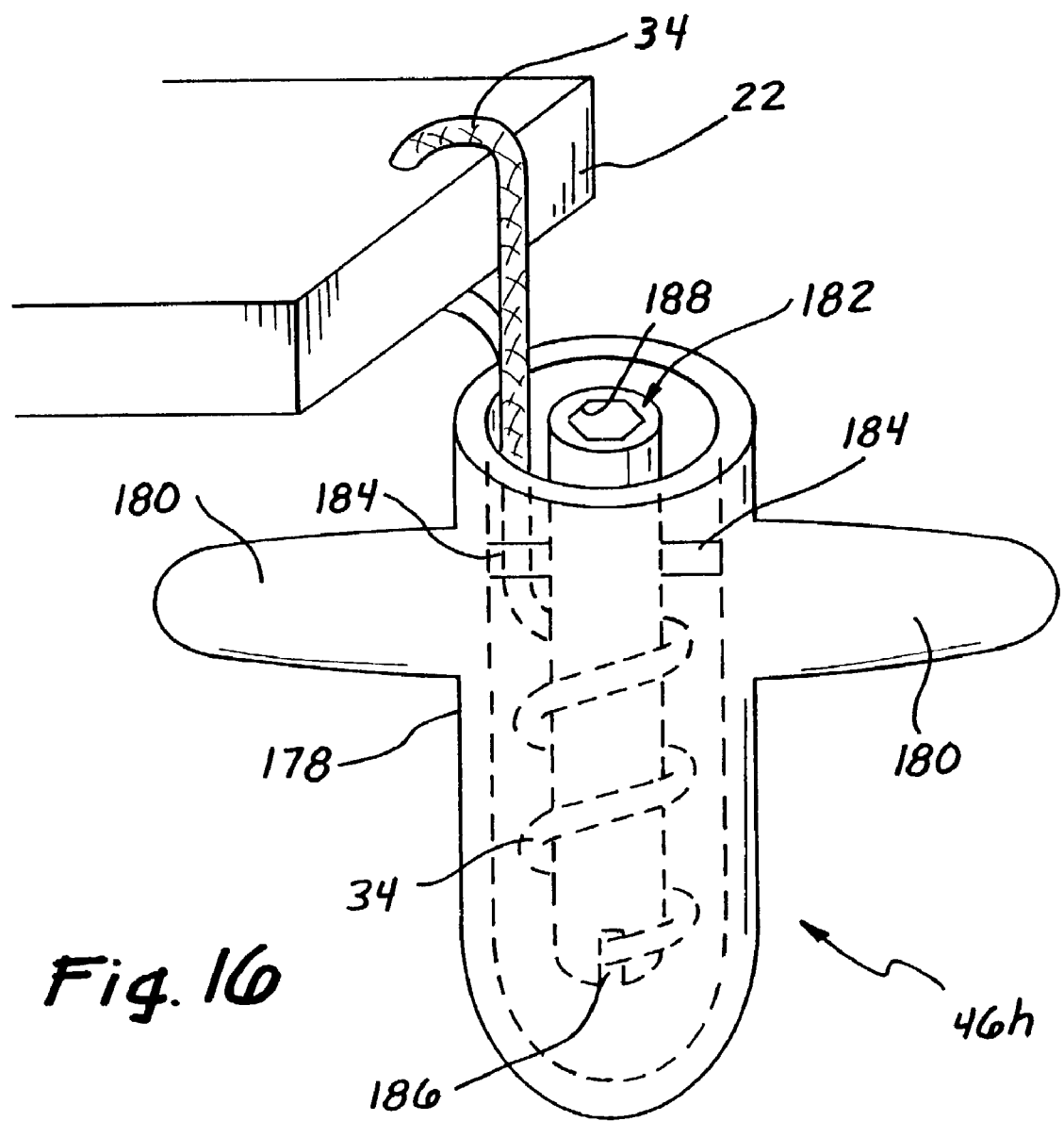
FIG. 16 is a perspective view of a vertical knotless bone and suture anchor which functions to wrap suture around a shaft in order to lock it in place.

In FIG. 16, there is shown yet another embodiment of a suture anchoring device 46h, which comprises a body 178, on which is disposed a plurality of sleeves 180 which are adapted to extend into adjacent cancellous bone (not shown), for anchoring the body within the bone. A core 182 is disposed within the body 178. Three fins 184 (two are shown) are disposed in an equally spaced fashion about the circumference of the body 178, between the core 182 and the inner surface of the body 178. Suture 34 is attached to soft tissue 22, such as a rotator cuff tendon (see FIGS. 1A–1F), and extends through the body 178, being wrapped about the core 182 along its length, as shown. One end of the suture 34 is attached to a distal end of the core 182 at an anchor point 186.

In operation, a driver (not shown) having a hex head engages a hexagonal aperture 188, and rotates the core 182, in order to further wrap the suture 34 about the core, and to thus tension the suture 34 and approximate the tendon 22 to adjacent bone (not shown). When the suture 34 is tensioned as desired, the core is rotationally locked in place, to thereby anchor the suture in place. During the tensioning step, the fins 184 function to snag the suture and to act as bearings for the core 182.

Figure 19:
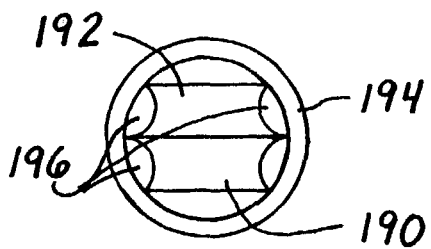
FIG. 19 is a cross-sectional view taken along lines 19—19 of FIG. 17.

Another embodiment of a suture anchoring device 46i is shown in FIGS. 17–20. The device comprises a first plate 190 and a second plate 192, with the first plate 190 being disposed beneath the second plate 192. In FIGS. 17 and 19, the device is shown in an undeployed state. The plates 190 and 192 are disposed within a hypotube 194. Welds 196 join the two plates. A length of suture 34 is threaded through the device 46i, as shown in FIG. 17, including apertures 198, 200, and 202 in the plates 190 and 192, respectively.

Figure 20:
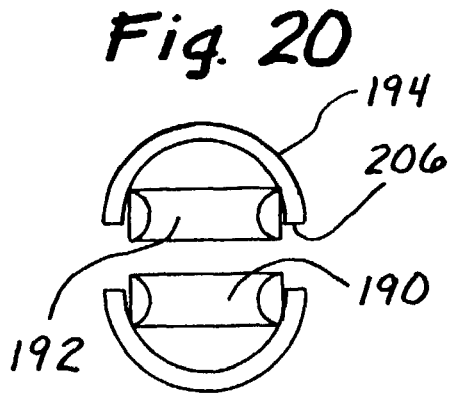
FIG. 20 is a cross-sectional view taken along lines 20—20 of FIG. 18.

As shown in FIGS. 18 and 20, to deploy the device 46i and anchor the suture 34, the upper plate 192 is retracted proximally, as shown by arrow 204. In the presently preferred embodiment, when a force in excess of 60 lb. is applied, the welds 196 fracture, thereby separating the plates 190, 192, and creating a space 206 therebetween. The axial displacement of the upper plate 192 relative to the lower plate 190 creates a tortuous path through the apertures 198, 200, and 202, as well as the space 206, through which the suture 34 traverses, thereby anchoring the suture in place.

Figure 21:
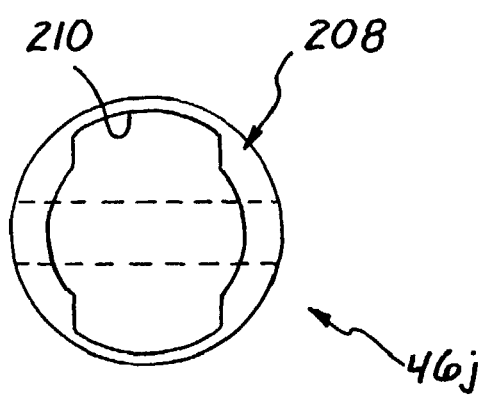
FIG. 21 is a cross-sectional view of still another embodiment of a suture anchoring device constructed in accordance with the principles of the present invention, showing the inventive device prior to insertion of a length of suture.
Figure 22:
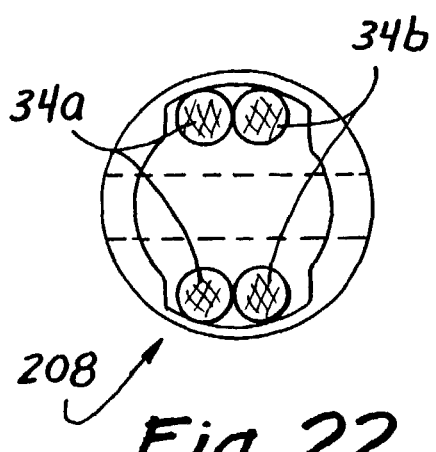
FIG. 22 is a cross-sectional view similar to that of FIG. 21, wherein suture is disposed within a cylinder comprising a portion of the inventive anchoring device.
Figure 23:
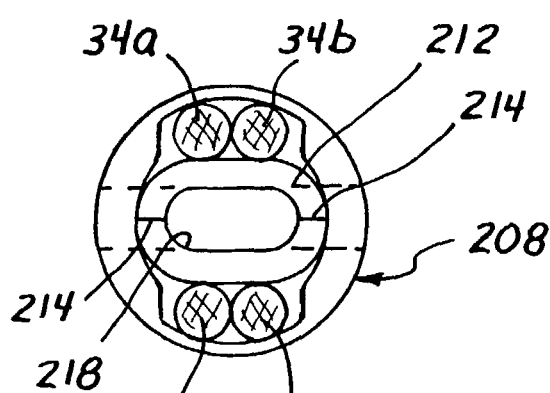
FIG. 23 is a cross-sectional view similar to those of FIGS. 21 and 22, wherein a second split tube has been inserted into the cylinder.

Yet another suture anchoring device 46j is shown in FIGS. 21–24. In this embodiment, there is provided an outer tube 208 having a lumen 210, as shown in FIG. 21, in cross-section. The tube 208 is disposed in a blind hole 40 within bone, as discussed in connection with previously disclosed embodiments. Suture lengths 34a, 34b are disposed through the lumen 210, as shown in FIG. 22, for attaching soft tissue 22 to bone 24. As in prior embodiments, each suture length extends distally through the lumen 210, about a suture return member, such as a pin (not shown), disposed at a distal end of the device 46j, and then extends proximally through the lumen and out of a proximal end of the device 46j. FIG. 23 illustrates a next step in the inventive sequence, wherein a tube 212 having a split 214 therein is introduced into the lumen 210, separating the proximally-extending legs of each suture length 34a, 34b from the distally-extending lengths of the same suture lengths. The tube 212 is formed of a suitable deformable or elastomeric biocompatible material. Then, once the suture 34a, 34b has been suitably tensioned to approximate the soft tissue 22 to the bone 24, a tapered actuation pin 216 (FIG. 24) is introduced distally into a lumen 218 of the split tube 212. Alternatively, the pin 216 could be pulled proximally through the lumen 218. This activity causes the outer diameter of the tube 212 to expand, because of separation at the split 214, as shown, thereby compressing, and thus anchoring the suture lengths 34a, 34b in place, as shown in FIG. 24.

Yet another embodiment of a suture anchoring device 46k is illustrated in FIGS. 25–26. In this embodiment, a tube 220 having a lumen 222 is disposed in a blind hole 40 within bone, as discussed in connection with previously disclosed embodiments. Suture lengths 34a, 34b are disposed through the lumen 222, as shown in FIG. 25, for attaching soft tissue 22 to bone 24. As in prior embodiments, and particularly as in the embodiment of FIGS. 21–24, each suture length extends distally through the lumen 222, about a suture return member, such as a pin (not shown), disposed at a distal end of the device 46k, and then extends proximally through the lumen and out of a proximal end of the device 46k. In this embodiment, a spring coil 224 is disposed axially through the lumen 222, again as shown in FIG. 25. Once the suture 34a, 34b has been tensioned as desired during the medical procedure, an actuation pin 226 (FIG. 26), similar to actuation pin 216, and preferably including a taper, is inserted through the spring coil 224, as shown, either proximally or distally, in order to expand the outer diameter of the spring coil 224, and thereby compress and anchor the sutures 34a, 34b in place.

Finally, another alternative suture anchoring embodiment 46l is illustrated in FIG. 27. This binding tapered thread anchor comprises an anchor body 228 adapted for disposition within a bone cavity 40, including bone anchor wings 230 for axially anchoring the body 228 within said cavity, as discussed in connection with prior embodiments. Suture lengths 34a, 34b extend distally through a center portion of the body 228, and continue about a suture return member or pin (not shown), extending proximally out of the body 228. The portions of suture lengths 34a and 34b which extend proximally out of the body 228 are not illustrated, for clarity. The interior wall 232 of the body 228 includes threads 234, and is tapered such that the interior diameter of the body 228 decreases in a distal direction, as shown. A tapered plug 236, having external threads 238 which complement the threads 234, and are adapted for engagement therewith, is adapted for disposition within the body 228, as shown in the figure. After the suture has been appropriately tensioned, as discussed in connection with prior embodiments, the plug 236 is threaded into the body 228, in order to create a zig-zag shaped binding lock on the suture 34, by forcing the suture ends 34a, 34b against the interior wall 232 of the body 228, such that the suture ends 34a, 34b are forced into the tortuous path created by the engaged threads 234, 238.

The apparatus and method of the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A suture anchoring device, comprising:
   an anchor body having an outer wall;
   a suture return member disposed at a distal end of said anchor body, for receiving a length of suture extending distally through said body, and returning a portion of said suture length in a proximal direction; and
   a passage extending along an interior surface of said wall for accommodating said length of suture, said passage tapering in width in a proximal to distal direction.

2. The suture anchoring device as recited in claim 1, and further comprising a plurality of internal threads disposed along said interior surface of said anchor body wall for forming said passage.

3. The suture anchoring device as recited in claim 2, and further comprising a plug having external threads which complement said internal threads, said plug being adapted for insertion into said anchor body so that said external threads and said internal threads are engaged.

4. The suture anchoring device as recited in claim 3, wherein said plug is tapered in a proximal to distal direction.

5. The suture anchoring device as recited in claim 3, wherein the threaded engagement creates a zig-zag shaped binding lock on the suture length received in said anchor body.

6. The suture anchoring device as recited in claim 1, and further comprising a member radially extending from said body for anchoring said device in adjacent bone.

7. A suture anchoring device, comprising:
an anchor body having an outer wall;
a lumen for accommodating a length of suture within said outer wall;
wherein an inner surface of said outer wall comprises threads; and
a tapered threaded plug adapted for insertion into said body, wherein said threads on said inner surface of said outer wall and threads on said tapered threaded plug engage to create a tortuous path for said length of suture in order to anchor said length of suture in place.

8. The suture anchoring device as recited in claim 7, and further comprising a member radially extending from said body for anchoring said device in adjacent bone.

9. A suture anchoring device, comprising:
an anchor body having a passage disposed therethrough, said anchor body having a proximal end and a distal end and said passage being defined by an interior wall of said anchor body, wherein the interior wall of the anchor body is tapered such that an interior diameter of the anchor body decreases in a distal direction; and
a plug adapted for insertion into said passage, said plug having an outer wall;
wherein said plug outer wall and said anchor body interior wall together define a path for receiving a length of suture therethrough.

10. The suture anchoring device as recited in claim 9, wherein said plug is tapered such that an external diameter of the plug decreases in a distal direction.

11. The suture anchoring device as recited in claim 9, wherein said anchor body interior wall includes internal threads.

12. The suture anchoring device as recited in claim 11, wherein said plug includes external threads thereon.

13. The suture anchoring device as recited in claim 12, wherein said internal and external threads are complementary, such that they engage one another when said plug is inserted into said anchor body, the engaged threads defining said path for receiving said length of suture therethrough, said path comprising a tortuous path for axially locking said length of suture in place.

14. The suture anchoring device as recited in claim 9, and further comprising a member radially extending from said body for anchoring said device in adjacent bone.

15. The suture anchoring device as recited in claim 9, and further comprising a suture return member disposed in proximity to the distal end of the anchor body, for receiving a length of suture extending distally through said body, and returning a portion of said suture length in a proximal direction.

16. A method for anchoring suture during a surgical repair procedure, comprising:
disposing a length of suture, which has been attached to a piece of soft tissue to be anchored to adjacent bone, through an anchor body having a passage extending therethrough in a distal direction;
disposing said length of suture about a suture return member located near a distal end of said anchor body, so that a portion of said length of suture extends back through said anchor body passage in a proximal direction; and
inserting a plug into said passage to lock said length of suture in place axially, wherein an interface between an external surface of said plug and an internal surface of said body, forming said passage, creates a tortuous path for said length of suture.

17. The method as recited in claim 16, wherein said external plug surface and said internal body surface both comprise threads, said interface comprising an engagement of said plug and body threads.

18. The method as recited in claim 16, wherein said interior body surface is tapered such that an interior diameter of the anchor body decreases in a distal direction and said plug is tapered such that an external diameter of the plug decreases in a distal direction.

19. A suture anchoring device, comprising:
an anchor body having a passage disposed therethrough, said anchor body having a proximal end and a distal end and said passage being defined by an interior wall of said anchor body;
a plug adapted for insertion into said passage, said plug having an outer wall;
wherein said plug outer wall and said anchor body interior wall together define a path for receiving a length of suture therethrough; and
a suture return member disposed in proximity to the distal end of the anchor body, for receiving a length of suture extending distally through said body, and returning a portion of said suture length in a proximal direction.

20. A method for anchoring suture during a surgical repair procedure, comprising:
disposing a length of suture, which has been attached to a piece of soft tissue to be anchored to adjacent bone, through an anchor body having a passage extending therethrough; and
inserting a plug into said passage to lock said length of suture in place axially, wherein an interface between an external surface of said plug and an internal surface of said body, forming said passage, creates a tortuous path for said length of suture;
wherein said interior body surface is tapered such that an interior diameter of the anchor body decreases in a distal direction and said plug is tapered such that an external diameter of the plug decreases in a distal direction.

* * * * *

Disclaimer

7,090,690 B2 - Seth A. Foerster, San Clemente, CA (US); Norman S. Gordon, Irvine, CA (US); Mark A. Ritchart, Murrieta, CA (US); Gregory H. Bain, Laguna Niguel, CA (US); George White, Corona, CA (US). DEVICES AND METHODS FOR REPAIRING SOFT TISSUE. Patent dated August 15, 2006. Disclaimer filed October 20, 2016, by the assignee, ArthroCare Corporation.

I hereby disclaim the following complete Claim 19 of said patent.

*(Official Gazette, January 6, 2026)*